United States Patent [19]

Mihashi et al.

[11] Patent Number: 5,633,694
[45] Date of Patent: May 27, 1997

[54] OPHTHALMOMETRIC APPARATUS FOR GENERATING AN IMAGE OF A SELECTION AND A SURFACE OF AN EYEGROUND OF A SUBJECT

[75] Inventors: Toshifumi Mihashi; Satoru Niimura; Katsuhiko Kobayashi, all of Tokyo, Japan

[73] Assignee: Kabushiki Kaisha Topcon, Tokyo, Japan

[21] Appl. No.: 509,337

[22] Filed: Jul. 31, 1995

[30] Foreign Application Priority Data

Jul. 31, 1994 [JP] Japan .................. 6-197853

[51] Int. Cl.$^6$ .......................................... A61B 3/10
[52] U.S. Cl. ..................... 351/211; 351/205; 351/221
[58] Field of Search .................... 351/221, 211, 351/220, 205, 200, 206

[56] References Cited

U.S. PATENT DOCUMENTS

| | | | |
|---|---|---|---|
| 5,141,302 | 8/1992 | Arai et al. | 351/221 |
| 5,387,951 | 2/1995 | Hatanaka | 351/221 |
| 5,459,570 | 10/1995 | Swanson et al. | |

*Primary Examiner*—Hung X. Dang
*Attorney, Agent, or Firm*—Brumbaugh, Graves, Donohue & Raymond

[57] ABSTRACT

The present invention relates to an ophthalmometric apparatus and is intended to provide an ophthalmometric apparatus that generates image signals representing a section of a measuring portion of a measuring eye. A first light source emits light rays having a comparatively short coherence length, a measuring optical system converges a light beam emitted by the first light source on a position substantially corresponding to the pupil of the measuring eye to illuminate a measuring portion, a beam splitter separates a reference optical path from the measuring optical path of the measuring optical system, a reference optical system including a reflecting mirror reflects a reference light beam, an interference optical system combines a reflected measuring light beam and a reflected reference light beam reflected by the reference optical system for interference, an image pickup device having a plurality of image sensing elements disposed in a substantially conjugate relation with the measuring portion receives an interference light beam provided by the interference optical system, an image signal generating unit generates image signals representing a section of the measuring eye from the output signals of the image pickup device when the reflecting mirror is shifted.

24 Claims, 16 Drawing Sheets

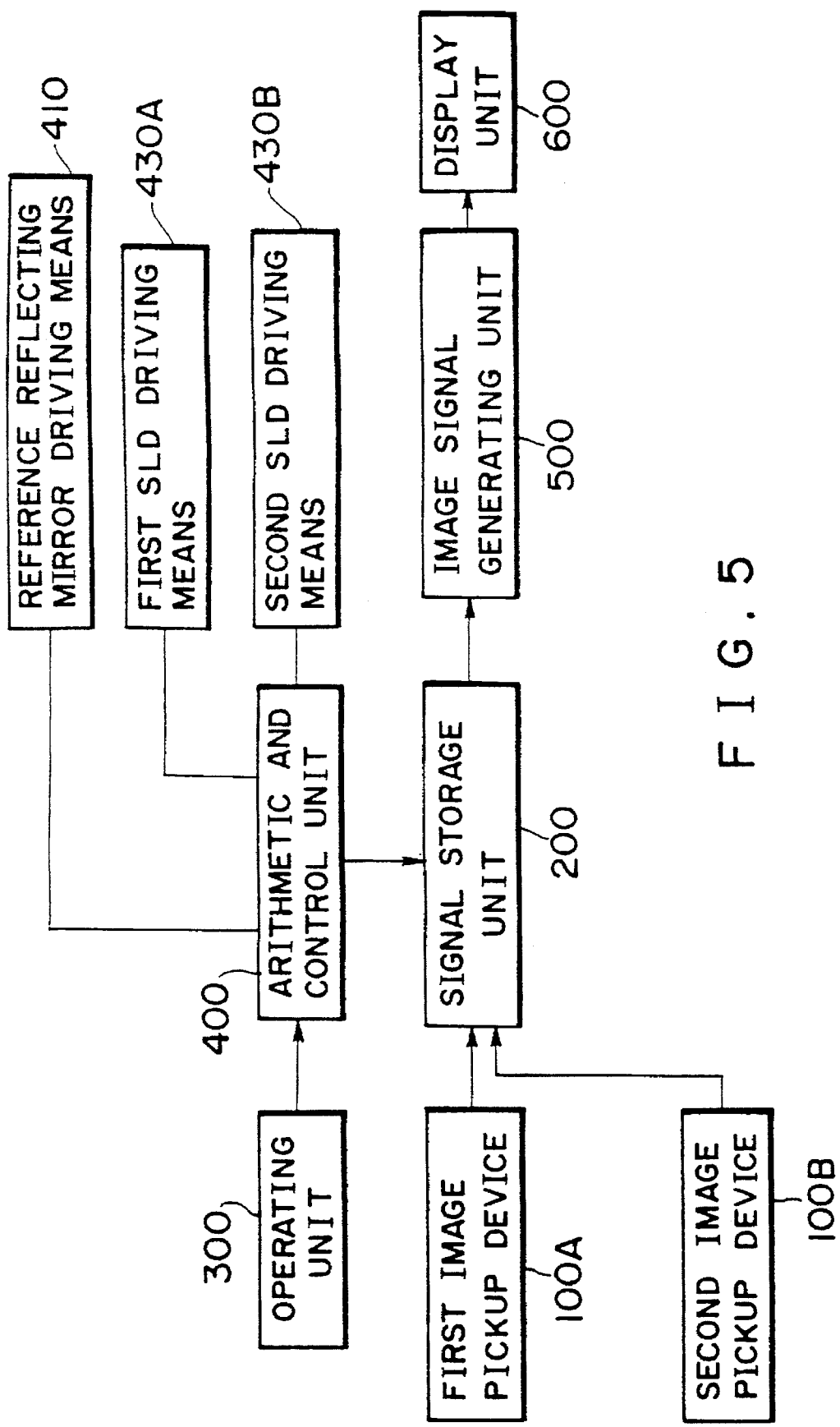
F I G. 5

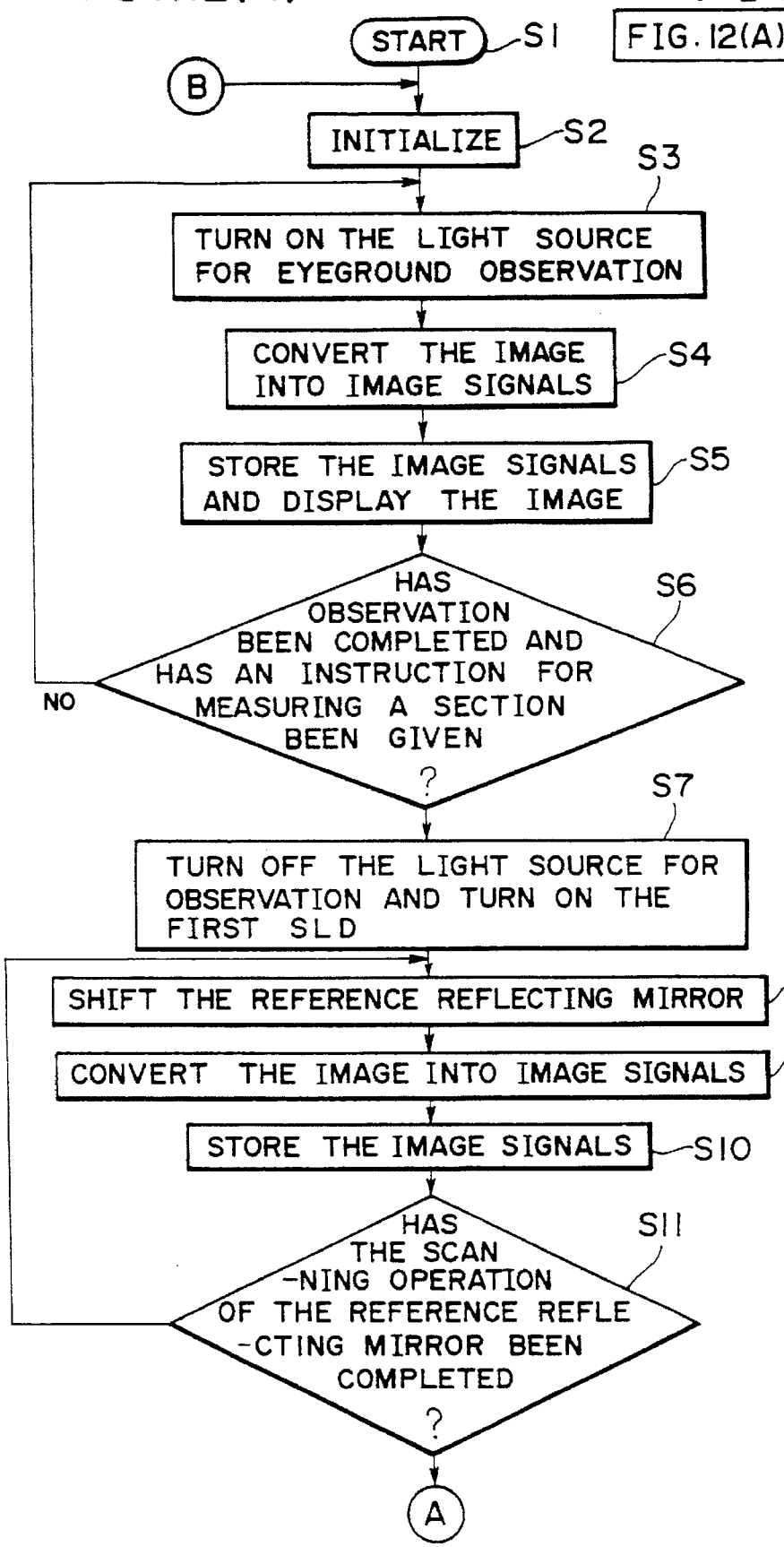

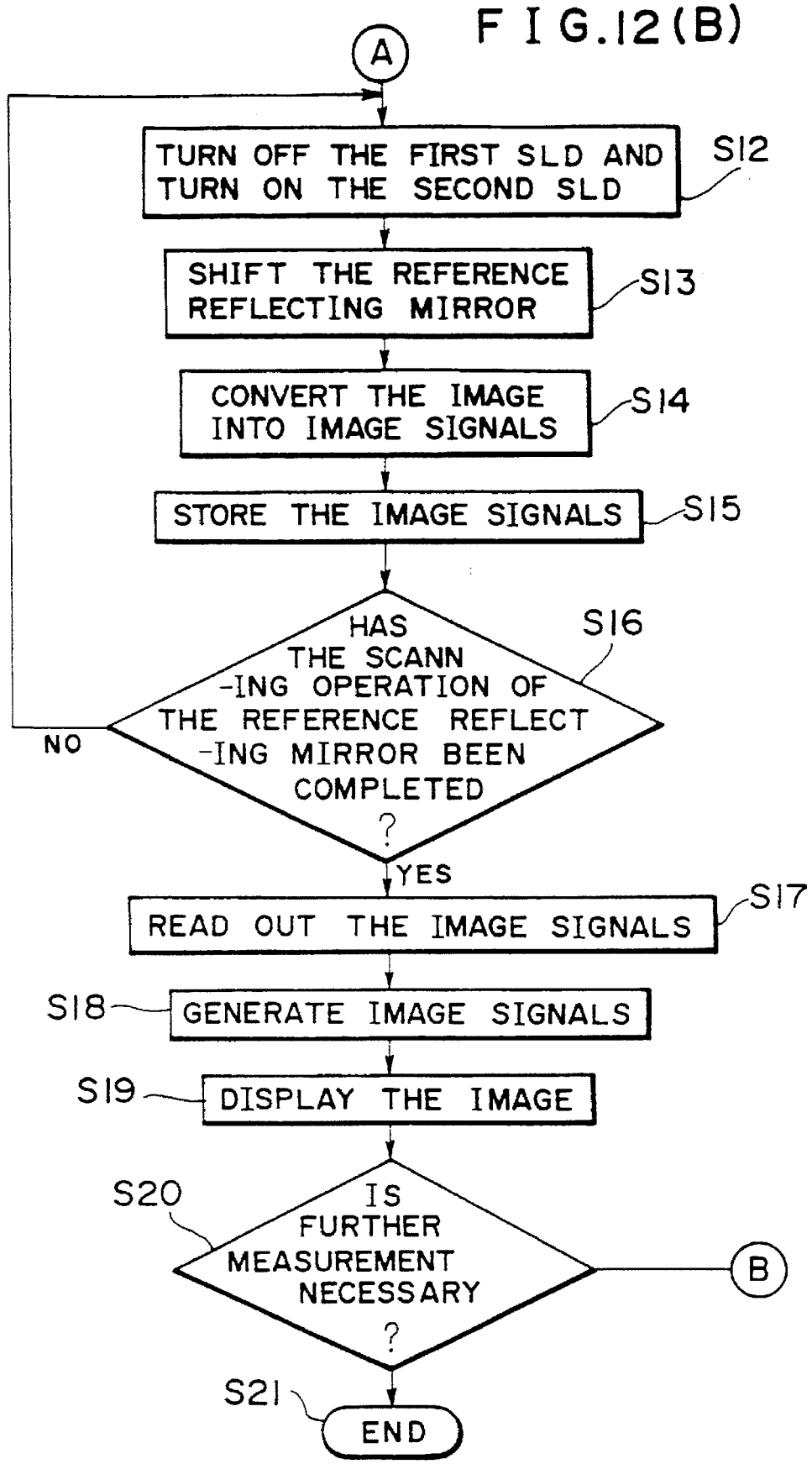

OPHTHALMOMETRIC APPARATUS FOR GENERATING AN IMAGE OF A SELECTION AND A SURFACE OF AN EYEGROUND OF A SUBJECT

BACKGROUND OF THE INVENTION

The present invention relates to an ophthalmometric apparatus and, more specifically, to an ophthalmometric apparatus capable of generating signals representing the image of a section of a measuring portion of a measuring eye.

A known technique of obtaining an sectional image of a measuring portion of the vivieye employs OCDR (optical coherence domain reflectometry). The OCDR employs a light source that emits light rays having a short coherence length, splits light rays emitted by the light source into a measuring light beam and a reference light beam, focuses the measuring light beam in a spot on the measuring portion, and varies the optical path length of the reference light beam.

The OCDR combines the reflected reference light beam and the measuring light beam to provide an interference signal, a reflecting mirror disposed on a reference optical path is moved to obtain interference signals and forms a sectional image of the measuring portion from the interference signals.

In this known OCDR, the data obtained by turning the reflecting mirror are only linear data parallel to the optical axis, and scanning must be performed in an X- and a Y-direction to obtain the data of three dimensions, which requires a comparatively long time. When measuring the vivieye, which is difficult to maintain stationary, the measurement must be carried out in a short measuring time.

When measuring a measuring portion, more specifically, a portion around the eyeground, it is desired to know which portion of the eyeground is being measured. However, the existing ophthalmometric apparatus are not necessarily able to meet such a requirement. Accordingly, there has been demand for an ophthalmometric apparatus capable of quickly measuring a measuring eye and of facilitating the confirmation of a measuring portion on the eyeground or the like.

BRIEF DESCRIPTION OF THE DRAWINGS

FIG. 5 is a block diagram showing the electrical configuration of the second embodiment;

FIGS. 12, 12A and 12B a flow chart of a program to be carried out by the third embodiment;

DESCRIPTION OF THE INVENTION

The present invention will be described hereinafter with reference to the accompanying drawings as applied to fundus cameras. When the eyeball is observed from outside, the comparatively simple outer wall of the eyeball including the sclera, the cornea, optic nerves, the blood vessels and such can be seen. The fundus can be seen when the eyeball is observed from inside through the pupil.

The fundus camera, which is used for examining the fundus, is indispensable for the diagnosis of diseases in the eyeground including retinal diseases, choroid diseases, optic neural diseases and the like. The fundus camera forms a photograph of the two-dimensional image of the eyeground or enables the real-time observation of the eyeground on a monitor.

The fundus camera in accordance with the present invention is an application of a coherence probe microscope and is a novel one developed specially for the observation of the eyeground. A coherence probe microscope is one type of scanning microscopes and uses a light source that emits light rays having a coherence length of about 20 μm.

First Embodiment

Figure 1:
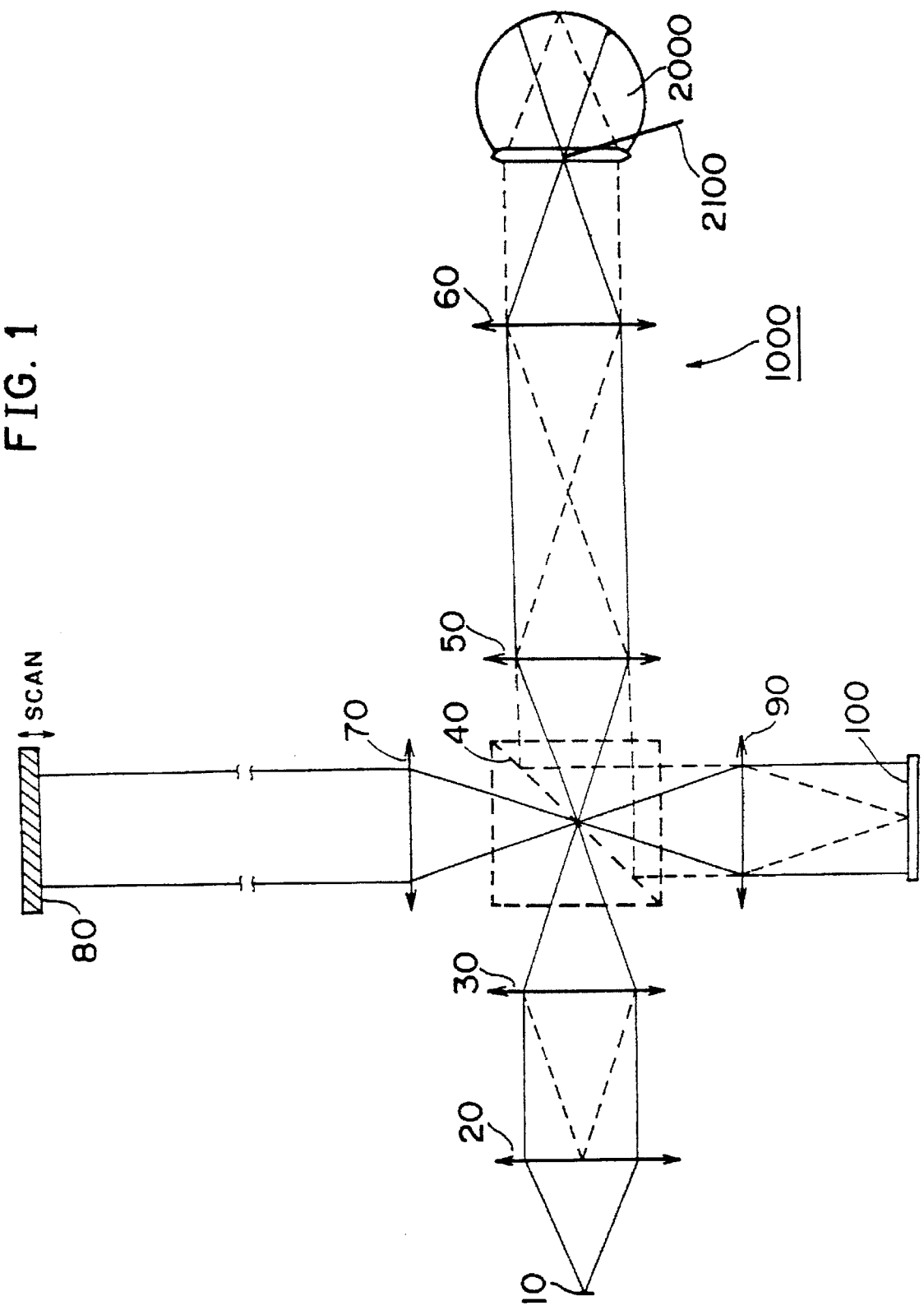
FIG. 1 is a diagrammatic view of an ophthalmometric apparatus in a first embodiment according to the present invention.

The basic construction of an interference optical apparatus 1000 in a first embodiment according to the present invention will be described with reference to FIG. 1. The interference optical apparatus 1000 comprises a interference optical beam system having light source 10, a first lens 20, a second lens 30, a beam splitter 40, a third lens 50, a fourth lens 60, a fifth lens 70, a reference reflecting mirror 80, a sixth lens 90 and an image pickup device 100.

The light source 10, i.e., a first light source, employed in the first embodiment emits light rays having a short coherence length. In view of requirements of the medical image of the eyeground and the signal-to-noise ratio of the interferometer during observation, the light source 10 is designed to emit light rays having a coherence length around 20 μm and not greater than 40 μm.

In the first embodiment, a superluminescence diode (SLD) is employed as the light source 10. The light source 10 may be any light emitting device other than the SLD, provided that the light emitting device is capable of emitting light rays having a suitable coherence length.

The relation between the coherence length, and the wavelength width of light emitted by the light source is expressed by:

$$\Delta K = \ln(2)(2/\pi)(\lambda 2/\Delta\lambda) \qquad (1)$$

where $\Delta K$ is the coherence length, $\lambda$ is the center wavelength of the light emitted by the light source, and $\Delta\lambda$ is the full width at half maximum of the light source.

The superluminescence diode (SLD) serving as the light source 10 of the first embodiment has λ=811 nm and Δλ=17.4 nm and hence, from expression (1), ΔK=16.68 μm.

Although a higher resolution is desirable in view of measuring accuracy, when the interference optical apparatus 1000 in the first embodiment is used for measuring the vivieye, the coherence length is reduced when resolution is enhanced and reduces the signal-to-noise ratio, i.e., the ratio of amplitude of detected signals to that of noise. Since signals from the vivieye are originally very weak, there is the possibility that measurement is impossible if the signal-to-noise ratio is small. Therefore, the coherence length of the light source 10 must be properly selected.

The light source 10 may be a light emitting device that emits light having a fixed specific wavelength width or may be a light emitting device that emits light having variable wavelength width and the wavelength width may be adjusted by a suitable means.

Interference optical beam system will be described hereinafter.

A measuring optical system comprises the first lens 20, the second lens 30, the beam splitter 40, the third lens 50 and the fourth lens 60. A reference optical system comprises the fifth lens 70 and the reference reflecting mirror 80.

Measuring Optical System

The first lens 20 and the second lens 30 converge a light beam emitted by the light source 10 on the beam splitter 40. The beam splitter 40 splits the light beam emitted by the light source 10 converged thereon by the first lens 20 and the second lens 30 into a light beam that travels toward the reference optical system including the reference reflecting mirror 80 and a light beam that travels toward the eye 2000, i.e., a measuring object.

The third lens 50 and the fourth lens 60 are disposed on an optical path between the beam splitter 40 and the eye 2000, i.e., a measuring object. The third lens 50 collimates the light beam passed through the beam splitter 40, and the fourth lens 60 focuses the light beam on the ocular lens (cornea) 2100 of the eye 2000, i.e., a measuring object.

The third lens 50 and the fourth lens 60 are disposed so that the distance between the third lens 50 and the fourth lens 60 is equal to the sum of their focal lengths due to restrictions on an optical path between the eyeground of the eye 2000 and an image pickup device.

Since the light beam traveled through the fourth lens 60 and fallen on the ocular lens (cornea) 2100 of the eye 2000 is focused on the pupil of the eye 2000 to enable Maxwellian view, the light beam is able to reach the eyeground of the eye 2000 without being affected by the refracting power of the ocular lens (cornea) 2100.

Reference Optical System

The light beam directed toward the reference reflecting mirror 80 by the beam splitter 40 is collimated by the fifth lens 70 and falls on the reference reflecting mirror 80.

The reference reflecting mirror 80 is positioned so that the optical path length between the beam splitter 40 and the reference reflecting mirror is basically equal to the optical path length between the beam splitter 40 and the eyeground of the eye 2000, i.e., a measuring object.

The reference reflecting mirror 80, i.e., a reflecting mirror unit, is scanned along the optical path for the observation of a three-dimensional shape or a section; that is, the reference reflecting mirror 80 is movable along the optical axis of the reference optical path.

The image pickup device 100 is disposed opposite to the reference reflecting mirror 80 with respect to the beam splitter 40, and the sixth lens 90 is disposed between the image pickup device 100 and the beam splitter 40.

The third lens 50, the fourth lens 60 and the sixth lens 90 are arranged so that the eyeground of the eye 2000 and the image pickup device 100 are in conjugate relation in terms of geometrical optics.

Interference Optical System

The interference optical system comprises the beam splitter 40 and the sixth lens 90 and combines the measuring reflected light beam of the measuring optical system and the reference reflected light beam of the reference optical system for interference.

The reflected light beam on the reference optical path and the reflected light beam on the measuring optical path are combined to make them interfere with each other.

That is, part of the reflected light on the reference optical path and part of the reflected light beam on the measuring optical path which have traveled the same optical path length interfere with each other to form an interference signal, and the interference signal is focused on the image pickup device 100 by the sixth lens 90; that is, only part of the reflected light beam reflected from a structure on the eyeground at an optical path length equal to an optical path length of the reference optical path including the optical path on the side of the reference reflecting mirror 80 contributes to interference.

Accordingly, as the reference reflecting mirror 80 moves along the optical axis, the reflecting portion of the eyeground contributing to interference changes accordingly. The depth range of portions of the eyeground contributing to interference is dependent on the coherence length of the light employed in measurement.

When the reference reflecting mirror 80 is moved for scanning, the wavelength of the reference light beam varies slightly due to Doppler effect and, consequently, the interference signal becomes a beat signal, and sectional image signal can be extracted by detecting the interference signal by a heterodyning technique.

Image Pickup Unit

The image pickup device 100 included in an image pickup unit has a plurality of light receiving elements disposed at positions substantially conjugate to the eyeground to receive the interference light beam formed by the interference optical system by interference.

Since the first embodiment is provided with the interference optical system, the two-dimensional data of a portion at a certain depth can be obtained by detecting interference fringes formed by moving the reference reflecting mirror 80 for scanning by the image pickup device 100. Three-dimensional data of a portion can be obtained by repeating measurement for different depths.

The image pickup device 100 may be a linear or a two-dimensional light sensor; the first embodiment employs a CCD linear sensor, i.e., a storage image pickup device. When it is desired to obtain three-dimensional data by using a linear image sensor as the image pickup device 100, the linear sensor is moved mechanically for scanning in directions perpendicular to the optical axis. In view of the type of the data thus obtained and time necessary for obtaining an image, it is desirable to use an optimum image sensor as the image pickup device 100.

The image sensor to be used as the image pickup device 100 need not be limited to a CCD sensor; any suitable image pickup device capable of measuring light reflected from points, such as an APD, may be used as the image pickup device 100.

Figure 2:
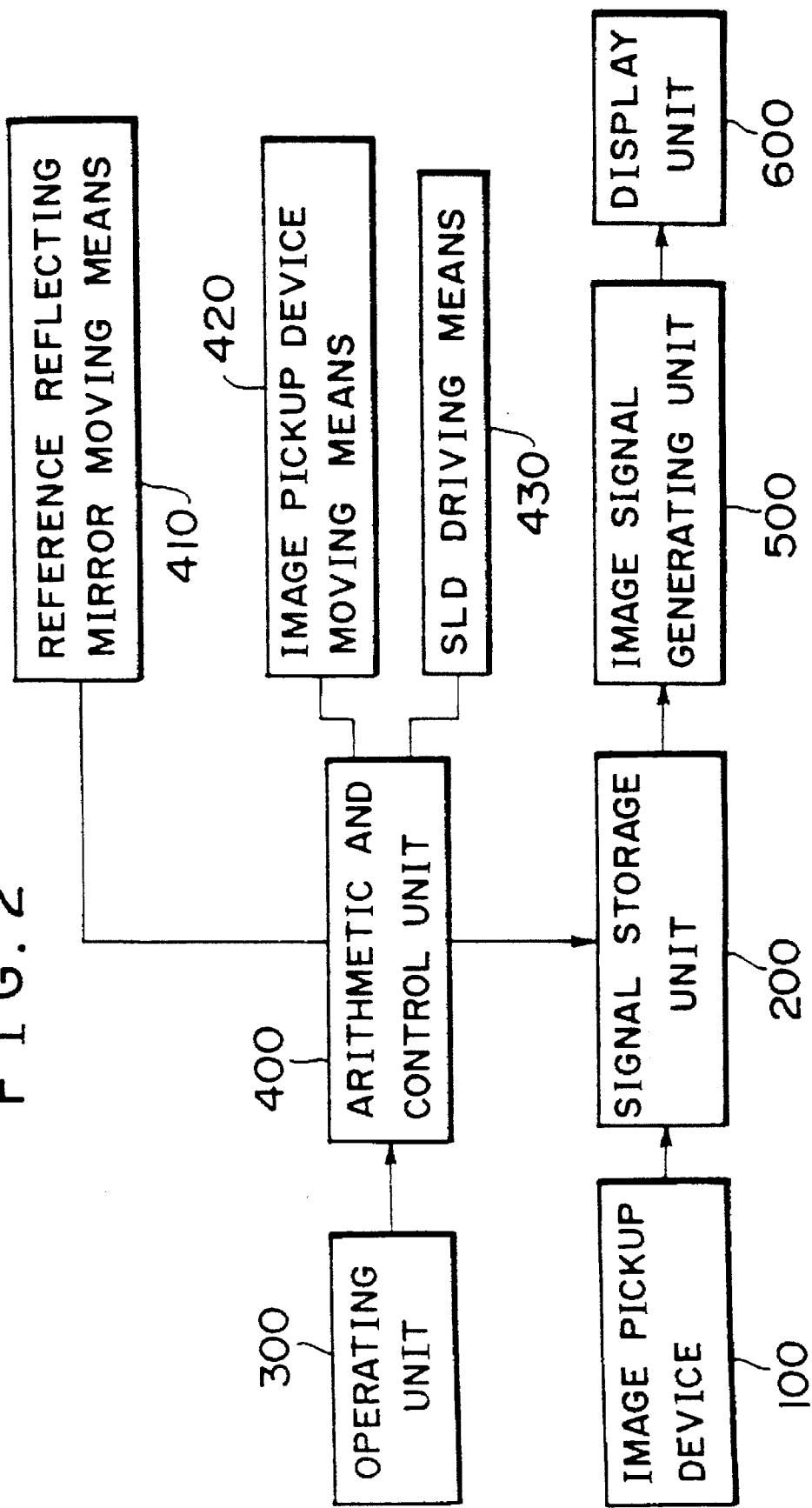
FIG. 2 is a block diagram of the electrical configuration of the first embodiment.

The electrical configuration of the first embodiment will be described hereinafter with reference to FIG. 2.

The interference optical apparatus 1000 in the first embodiment has an electrical system comprising the image pickup device 100, a signal storage unit 200, an operating unit 300, an arithmetic and control unit 400, an image signal generating unit 500 and a display unit 600.

The signal storage unit 200 stores image signals representing interference fringes and such detected by the image pickup device 100.

The operating unit 300 is operated by the operator of the interference optical apparatus 1000 to enter desired instructions.

The arithmetic and control unit 400 controls the general operations of the interference optical apparatus 1000, particularly, the operations of the light source 10 and the reference reflecting mirror 80. Connected to the arithmetic and control unit 400 are a reference reflecting mirror moving means 410, an image pickup device moving means 420 and an SLD driving means 430.

The reference reflecting mirror moving means 410 moves the reference reflecting mirror 80 along the optical axis by a distance according to a driving signal provided by the arithmetic and control unit 400. The image pickup device moving means 420 moves the image pickup device 100 in a direction perpendicular to a direction along which the elements of the image pickup device 100 are arranged by a distance according to a driving signal provided by the arithmetic and control unit 400. The reference reflecting mirror moving means 410 and the image pickup device moving means 420 are suitable linear moving mechanisms.

The SLD driving means 430 drives the light source 10, i.e., the SLD, so as to emit light having a short coherence length.

The image signal generating unit 500 generates image signals representing a sectional image of the eyeground on the basis of the output signals of the image pickup device 100 when the reference reflecting mirror 80 is moved.

The display unit 600 comprises a display or the like, and displays an image represented by the image signals of the sectional image of the eyeground provided by the image signal generating unit 500.

Figure 3:
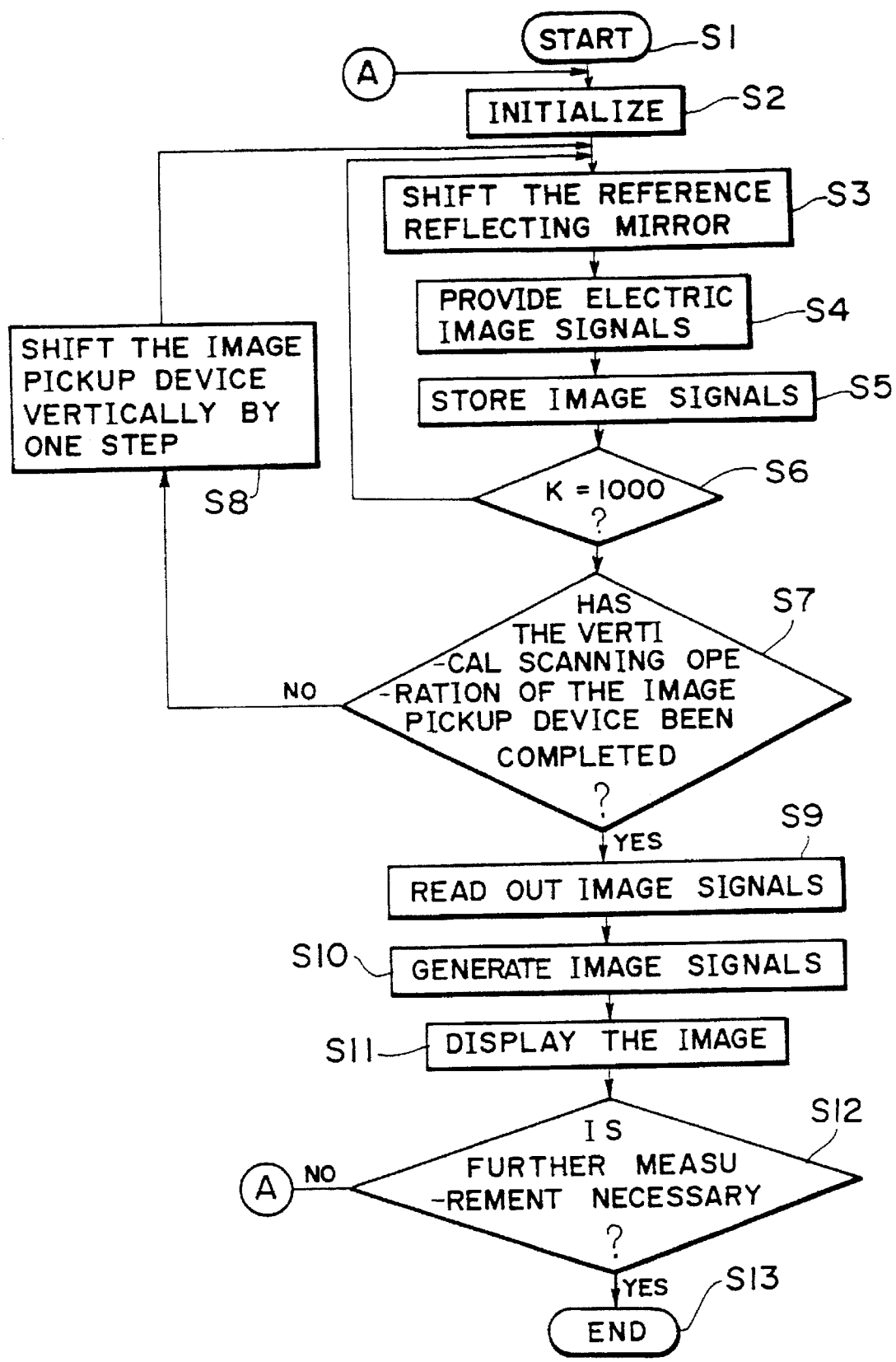
FIG. 3 is a flow chart of a program to be carried out by the first embodiment.

The operation of the first embodiment will be described hereinafter with reference to FIG. 3.

In step S1, the operating unit 300 is operated to actuate the arithmetic and control unit 400, and then the interference optical apparatus 1000 starts photographing the eyeground.

In step S2, the interference optical apparatus 1000 is initialized to prepare for measurement. In the following description, a Z-axis extends along the depth of the eyeground, an X-axis extends perpendicularly to the Z-axis and parallel to the arrangement of the image sensing elements of the image pickup device 100, i.e., a linear image sensor, and a Y-axis extends perpendicularly to the X-axis parallel to the arrangement of the image sensing elements.

The number of the image sensing elements of the image pickup device 100 is i. When used as a suffix, i=1 to 256 in the first embodiment. The image pickup device 100 can be moved by the image pickup device moving means 420 along the Y-axis in steps j from 1 to 511 in the first embodiment.

The reference reflecting mirror 80 can be moved by the reference reflecting mirror moving means 410 in steps k from 1 to 1000 in the first embodiment.

When the width of steps is half the wavelength of the measuring light or below, the waveforms of fringe scan can be reproduced from detection signals.

In step S3, the arithmetic and control unit 400 drives the reference reflecting mirror moving means 410 to position the reference reflecting mirror 80 at a position corresponding to k=1, i.e., a measurement starting position.

Then, in steps S4, the image pickup device 100 converts an interference image formed when the reference reflecting mirror 80 is positioned at the position corresponding to k=1 into electric signals. Since the image pickup device 100 in the first embodiment is a linear sensor, image data of portions represented by coordinates $(X_i, Y_1, Z_1)$, where i=1 to 256, can be obtained. Therefore, the data obtained with the reference reflecting mirror 80 positioned at the measurement starting position can be expressed by $(L_{x1y1z1}, L_{x2y1z1}, L_{x3y1z1}, \ldots, L_{x255y1z1}, L_{x256y1z1})$.

In step S5, the arithmetic and control unit 400 stores the image sisals obtained in step S4 in the signal storage unit 200.

In step S6, a query is made to see if k=1000. If k≠1000, k is incremented by one and the program returns to step S3. Then, in step S3, the arithmetic and control unit 400 drives the reference reflecting mirror moving means 410 to shift the reference reflecting mirror 80 to a position corresponding to k=2. Since the reference reflecting mirror 80 is shifted along the optical axis, the reflecting portion of the eyeground contributing to interference shifts in the direction of the depth, a different interference image can be obtained and, consequently, the image pickup device 100 is able to obtain image data expressed by $(X_i, Y_1, Z_2)$, where i=1 to 256, i.e., $(L_{x1y1z2}, L_{x2y1z2}, L_{x3y1z2}, \ldots, L_{x255y1z2}, L_{x256y1z2})$.

Similarly, steps S3 to S6 are repeated to shift the reference reflecting mirror 80 sequentially to positions corresponding to k=3 to 1000 and the image data thus obtained is stored in the signal storage unit 200.

If k=1000 in step S6, a query is made in step S7 to see if j=512. If j≠511, j is incremented by one, and the the arithmetic and control unit 400 drives the image pickup device moving means 420 in step S8 to shift the image pickup device 100 by one step along the Y-axis.

When the width of steps along the Y-axis is substantially equal to the effective light receiving range of the CCD, the data do not overlap each other and continuous data along the Y-axis can be obtained.

After the image pickup device 100 has been shifted in step S8, the program returns to step S3, and the image pickup device 100 is able to obtain image data of portions at positions represented by coordinates $(X_i, Y_2, Z_1)$, where i=1 to 256, i.e., $(L_{x1y2z1}, L_{x2y2z1}, L_{x3y2z1}, \ldots L_{x255y2z1}, L_{y256y2z1})$.

The measurement is repeated until the reference reflecting mirror 80 is shifted to a position corresponding to k=1000, and image data up to $(L_{x1y2z1000}, L_{x2y2z1000}, L_{x3y2z1000}, \ldots, L_{x255y2z1000}, L_{x256y2z1000})$ is stored in the signal storage unit 200.

If j=512 in step S7, step S9 is executed. A series of measuring steps for obtaining image data is completed, and image data from $(L_{x1y1z1}, L_{x2y1z1}, L_{x3y1z1}, \ldots, L_{x255y1z1}, L_{x256y1z1})$ to $(L_{x1y512z1000}, L_{x2y512z1000}, L_{x3y512z1000}, \ldots, L_{x255y512z1000}, L_{x256y512z1000})$ is stored in the signal storage unit 200.

In step S9, the operating unit 300 is operated to make the arithmetic and control unit 400 read out the image signals from the signal storage unit 200.

The arithmetic and control unit 400 is capable of sending the image data stored in the signal storage unit 200 in optional order instead of order of storage of the image data to the image signal generating unit 500.

For example, when it is desired to display an image of a section of the eyeground along the Z-axis on the display unit 600, the image data is sent out in order of ($L_{x1y1z1}$, $L_{x1y1z2}$, $L_{x1y1z3}$, . . . , $L_{x1y1z255}$, $L_{x1y1z256}$), ($L_{x2y1z1}$, $L_{x2y1z2}$, $L_{x2y1z3}$, . . . , $L_{x2y1z255}$, $L_{x2y1z256}$).

In step S10, the image signal generating unit 500 generates image signals of intensities respectively corresponding to the magnitudes of the data fetched from the signal storage unit 200, and then gives the image signals to the display unit 600 in step S11. The display unit 600 is capable of displaying a sectional image of a portion taken along the Z-axis, a sectional image of a portion taken along the Y-axis or a perspective image of a portion according to an instruction given thereto by the operator. A generally known three-dimensional image displaying technique can be used for displaying the image.

In step S12, a query is made to see if further measuring operation is necessary. The program returns to step S2 if the response in step S12 is affirmative or the program goes to step S13 to end the measuring operation.

Second Embodiment

The first embodiment is provided with the single light source 10 and displays sectional images and the like of structures around the retina. An interference optical apparatus 1000 in a second embodiment according to the present invention is provided with two light sources 10A and 10B that emit light beams of different wavelengths, respectively, and carries out spectroscopic measurement to display images of structures around the retina.

Figure 4:
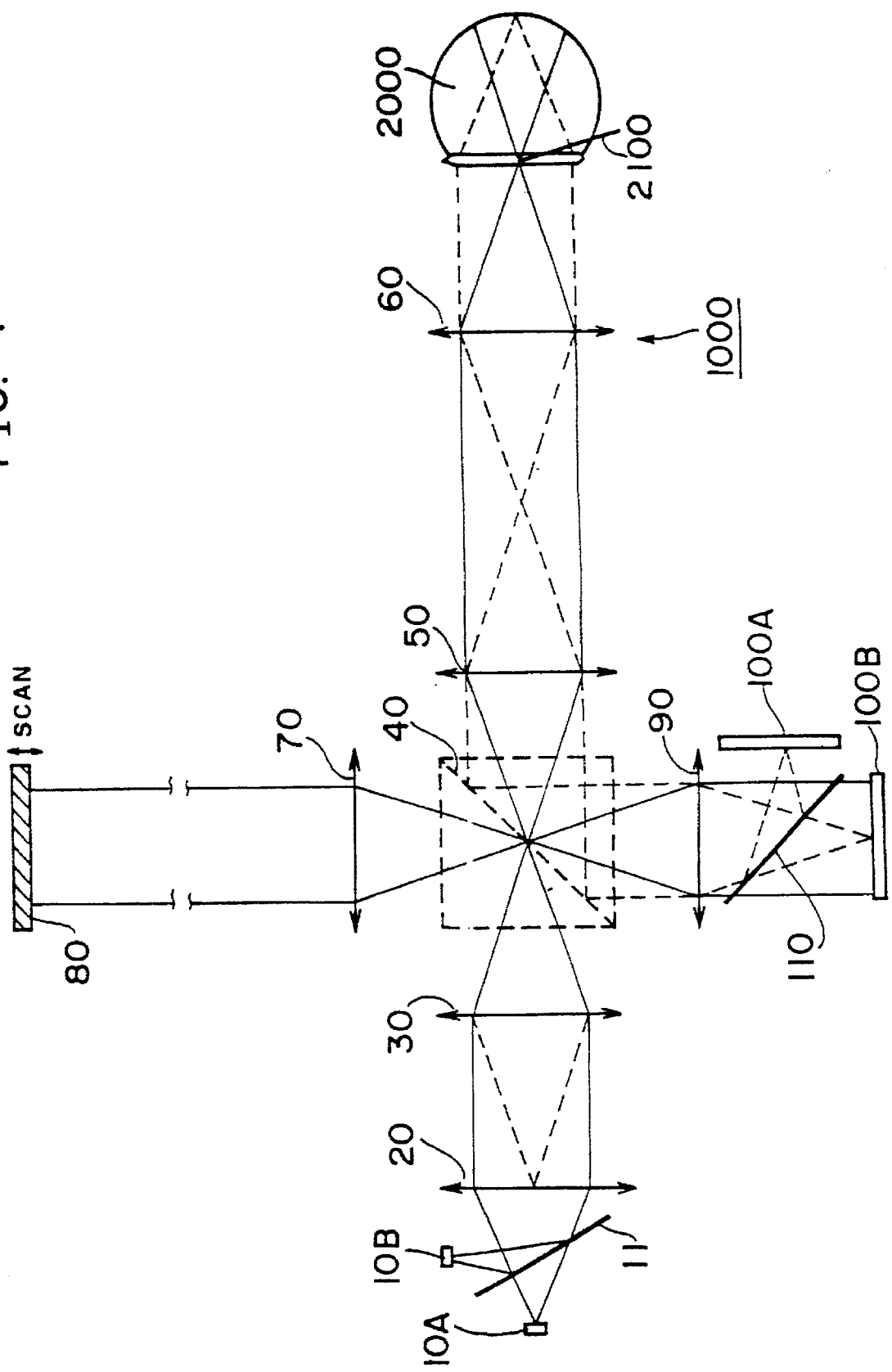
FIG. 4 is a diagrammatic view of an ophthalmometric apparatus in a second embodiment according to the present invention.

The basic construction of the interference optical apparatus in the second embodiment will be described with reference to FIG. 4. The interference optical apparatus 1000 in the second embodiment comprises a light source 10A, a light source 10B, a first dichroic mirror 11, a first lens 20, a second lens 30, a beam splitter 40, a third lens 50, a fourth lens 60, a fifth lens 70, a reference reflecting mirror 80, a sixth lens 90, a first image pickup device 100A, a second image pickup device 100B and a second dichroic mirror 110.

The light source 10A (light source 1A) emits light having a short coherence length. The light source 10A employed in the second embodiment is a superluminescence diode (SLD) that emits light having a desired coherence length.

The light source 10B (light source 1B) emits light having a short coherence length. The light source 10B employed in the second embodiment is a superluminescence diode (SLD) that emits light having a desired coherence length.

The respective wavelengths of light beams to be emitted by the light sources 10A and 10B must be selectively determined so that the transmittances of the light beams to the component substances of the eye including the cornea, the aqueous humor, the lens and the vitreous body are not extremely small. Generally, according to the spectral transmittance distribution of light rays transmitted by the eye, the transmittances of light rays of wavelength of 0.4 µm or below and 1.4 µm or above are very small. Therefore, the light source 10A employs an SLD that emits light rays of a wavelength of about 0.8 µm, and the light source 10B employs an SLD that emits light rays of a wavelength of about 1.1 µm.

The light sources 10A and 10B are disposed so that the light sources 10A and 10B are in conjugate relation in terms of geometrical optics with respect to the first lens 20.

The first dichroic mirror 11 combines the light beams emitted respectively by the light sources 10A and 10B.

The beam splitter 40 transmits the 0.8 µm wavelength light beam emitted by the light source 10A and reflects the 1.1 µm wavelength light beam emitted by the light source 10B.

In the second embodiment, the first image pickup device 100A and the second image pickup device 100B employ CCD area sensors, i.e., storage image sensors. Therefore, the image pickup devices 100A and 100B need not be moved, whereas the image pickup device 100 of the first embodiment needs to be moved along the Y-axis by the image pickup device moving means 420.

The second dichroic mirror 110 separates the light beams emitted by the light sources 10A and 10B. Interference fringes formed by the light beam emitted by the light source 10A are converted into image signals by the first image pickup device 100A, interference fringes formed by the light beam emitted by the light source 10B are converted into image signals by the second image pickup device 100B.

The construction of the optical system of the second embodiment is the same in other respects as that of the first embodiment, and hence the description thereof will be omitted.

The electrical configuration of the second embodiment will be described hereinafter with reference to FIG. 5.

The interference optical apparatus 1000 in the second embodiment has an electrical system comprising the first image pickup device 100A, the second image pickup device 100B, a signal storage unit 200, an operating unit 300, an arithmetic and control unit 400, an image signal generating unit 500 and a display unit 600.

The signal storage unit 200 stores image signals of interference fringes received by the first image pickup device 100A and the second image pickup device 100B.

The arithmetic and control unit 400 controls the general operations of the interference optical apparatus 1000, particularly, the operations of the light sources 10A and 10B and the reference reflecting mirror 80.

Connected to the arithmetic and control unit 400 are a reference reflecting mirror moving means 410, a first SLD driving means 430A and a second SLD driving means 430B.

The first SLD driving means 430A drives the light source 10A to make the light source 10A emit a light beam having a wavelength of about 0.8 µm, and the second SLD driving means 430B drives the light source 10B to make the light source 10B emit a light beam having a wavelength of about 1.1 µm.

The electrical configuration of the second embodiment is the same in other respects as that of the first embodiment, and hence the description thereof will be omitted.

Figure 6:
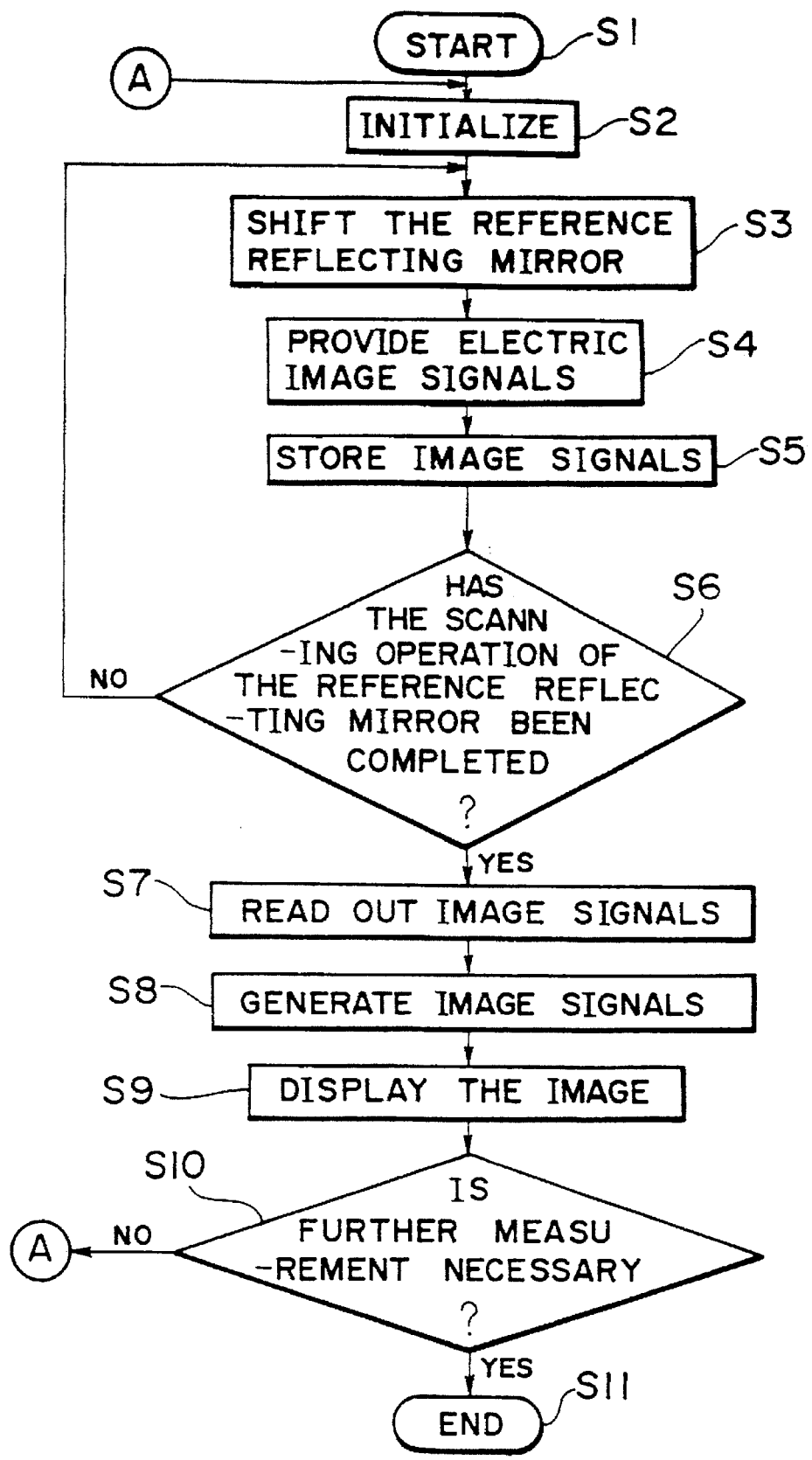
FIG. 6 is a flow chart of a program to be carried out by the second embodiment.

The operation of the second embodiment will be described hereinafter with reference to FIG. 6.

In step S1, the operating unit 300 is operated to actuate the arithmetic and control unit 400, and then the interference optical apparatus 1000 starts photographing the eyeground.

In step S2, the interference optical apparatus 1000 is initialized to prepare for measurement. In the following description, a Z-axis extends along the depth of the eyeground. Each of the first image pickup device 100A and the second image pickup device 100B, which are area image sensors, has image sensing elements arranged along an X- and a Y-axis which are perpendicular to the Z-axis.

The number of the image sensing elements of each of the first image pickup device 100A and the second image pickup device 100B arranged on each of lines parallel to the X-axis is i, and the number of image sensing elements arranged on each of rows parallel to the Y-axis is j. When used as suffixes, i=1 to 236 and j=1 to 511.

The reference reflecting mirror 80 can be moved by the reference reflecting mirror moving means 410 in steps k from 1 to 1000 in the second embodiment.

In step S3, the arithmetic and control unit 400 drives the reference reflecting mirror moving means 410 to position the reference reflecting mirror 80 at a position corresponding to k=1, i.e., a measurement starting position.

Then, in steps S4, the first image pickup device 100A converts an interference image formed by the light beam emitted by the light source 10A when the reference reflecting mirror 80 is positioned at the position corresponding to k=1 into electric signals. Since the first image pickup device 100A in the second embodiment is an area sensor, image data of portions represented by coordinates $(X_i, Y_j, Z_1)$, where i=1 to 256 and j=1 to 511, can be obtained.

Similarly, the second image pickup device 100B converts an interference image formed by the light beam emitted by the light source 10B when the reference reflecting mirror 80 is positioned at the position corresponding to k=1 into electric signals.

In step S5, the arithmetic and control unit 400 stores the image signals obtained in step S4 in the signal storage unit 200.

In step S6, a query is made to see if k=1000. If k≠1000, k is incremented by one and the program returns to step S3. Then, in step S3, the arithmetic and control unit 400 drives the reference reflecting mirror moving means 410 to shift the reference reflecting mirror 80 to a position corresponding to k=2. Since the reference reflecting mirror 80 is shifted along the optical axis, the reflecting portion of the eyeground contributing to interference shifts in the direction of the depth, a different interference image can be obtained.

Consequently, the first image pickup device 100A and the second image pickup device 100B are able to obtain image data expressed by $(L_i, Y_j, Z_2)$, where i=1 to 256 and j=1 to 511.

Similarly, steps S3 to S6 are repeated to shift the reference reflecting mirror 80 sequentially to positions corresponding to k=3 to 1000 and the image data thus obtained is stored in the signal storage unit 200.

If k=1000 in step S6, step S7 is executed. At this stage a series of image data measuring operations is completed and image data from $(L_{x1y1z1}, L_{x2y1z1}, L_{x3y1z1}, \ldots, L_{x255y1z1}, L_{x256y1z1})$ to $(L_{x1y512z1000}, L_{x2y512z1000}, L_{x3y512z1000}, \ldots, L_{x255y512z1000}, L_{x256y512z1000})$ is stored in the signal storage unit 200.

First image data is obtained by the first image pickup device 100A and second image data is obtained by the second image pickup device 100B.

In step S7, the operating unit 300 is operated to make the arithmetic and control unit 400 read out the image signals from the signal storage unit 200.

The arithmetic and control unit 400 is capable of sending the image data stored in the signal storage unit 200 in optional order instead of order of storage of the image data to the image signal generating unit 500.

For example, when it is desired to display an image of a section of the eyeground along the Z-axis on the display unit 600, the image data is sent out in order of $(L_{x1y1z1}, L_{x1y1z2}, L_{x1y1z3}, \ldots, L_{x1y1z255}, L_{x1y1z256})$, $(L_{x2y1z1}, L_{x2y1z2}, L_{x2y1z3}, \ldots L_{x1y1z255}, L_{x2y1z256})$. In step S8, the image signal generating unit 500 generates image signals of intensities respectively corresponding to the magnitudes of the data fetched from the signal storage unit 200, and then gives the image signals to the display unit 600 in step S9. The display unit 600 is capable of displaying a sectional image of a portion taken along the Z-axis, a sectional image of a portion taken along the Y-axis or a perspective image of a portion according to an instruction given thereto by the operator. A generally known three-dimensional image displaying technique can be used for displaying the image.

In step S10, a query is made to see if further measuring operation is necessary. The program returns to step S2 if the response in step S10 is affirmative or the program goes to step S11 to end the measuring operation.

Using the two light sources 10A and 10B that emit light rays of different wavelengths, respectively, the second embodiment thus constructed is able to display the characteristics of spectral distribution around the retina.

Figure 7:
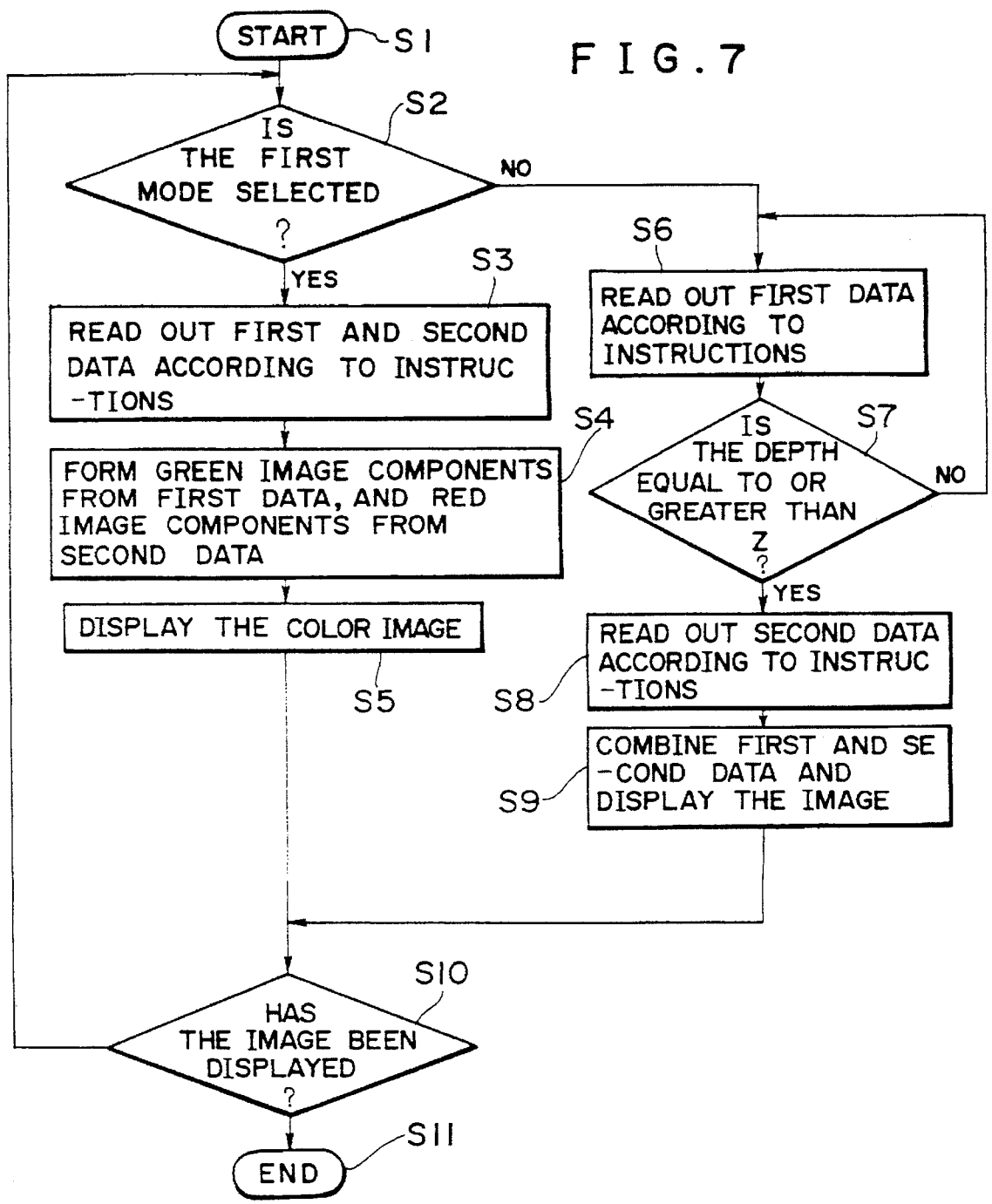
FIG. 7 is a flow chart of a program to be carried out by the second embodiment.

An image displaying method by which the second embodiment displays images will be described concretely with reference to FIG. 7. An image displaying program is started in step S1. In step S2, a query is made to see if a first mode is selected by operating the operating unit 300.

If the response in step S2 is affirmative, i.e., when the first mode is selected, the first data obtained by the first image pickup device 100A and the second data obtained by the second image pickup device 100B are read in step S3; that is, two groups of image data are provided for the same portion of the eyeground. In step S4, green image components are formed by using the first data obtained by using the light beam having the shorter wavelength, and red image components are formed by using the second data obtained by using the light beam having the longer wavelength, and a color image is displayed in step S5.

Figure 8:
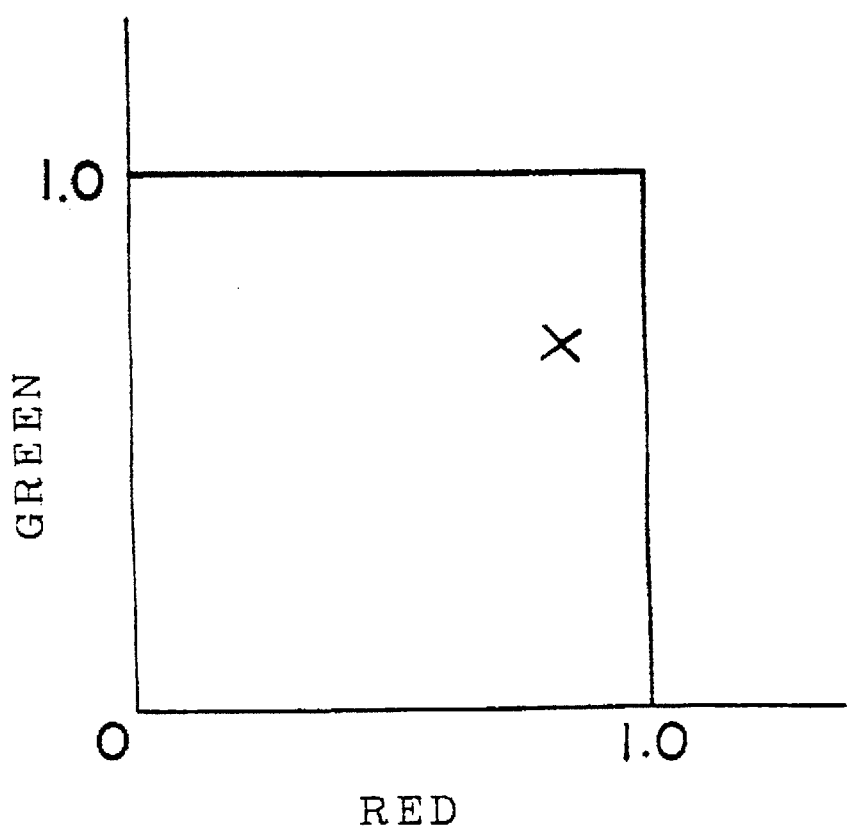
FIG. 8 is a diagram of assistance in explaining a first mode of the second embodiment.

As shown in FIG. 8 in which the green image components are measured on the vertical axis and the red image components are measured on the horizontal axis, when a color image is displayed in the first mode, the respective reflectances of the two light beams having different wavelengths can be discriminated from each other by color. Therefore, specified portions of the sectional image of the measuring eye can be simply and exactly discriminated from each other and, consequently, the composition of a portion around the retina can be minutely observed.

The green image components represented by the first data obtained by using the light beam having the shorter wavelength correspond to first color signals, and the red image components represented by the second data obtained by using the light beam having the longer wavelength correspond to second color signals.

When the response in step S2 is negative, i.e., when a second mode is selected, the first data is read in step S6.

The light beam having the longer wavelength, as compared with the light beam having the shorter wavelength, is capable of penetrating into the depth of the retina. Therefore, it is desirable to use the first data obtained by using the light beam having the shorter wavelength to represent portions to a certain depth of the retina and to use the second data obtained by using the light beam having the longer wavelength to represent portions beyond the certain depth of the retina.

In step S7, a query is made to see if a depth from the retina correspond to Z corresponding to a given depth from the retinal. Steps S6 is repeated to use the first data until the depth reaches Z. When the response in step S7 is affirmative, the program goes to step S8 to use the second data.

In step S9, the first data corresponding to a portion from the retina to the depth corresponding to Z, and the second data corresponding to a portion in depth beyond the depth corresponding to Z are combined to form an image to be displayed, and the image is displayed by the display unit 600.

After displaying the image in steps S5 to S9, a query is made in step S10 to see if the display of the image has been completed. When the operating unit 300 is operated to enter a display completion instruction, the program is ended in step S11.

If the response in step S10 is negative, the program returns to steps S2.

The first data representing the portion from the retina to the depth corresponding to Z corresponds to the image signals representing a section of the front half of the measuring eye, and the second data representing the portion beyond the depth corresponding to Z corresponds to the image signals representing the back half of the measuring eye.

Third Embodiment

A third embodiment is a fundus camera 3000 with a coherence probe, capable of functioning as both a fundus camera and a coherence three-dimensional measuring apparatus and of measuring portions at measuring positions simultaneously.

Therefore the third embodiment has an optical system for observing the eyeground, i.e., an eyeground image optical system and an interferometer forming a coherence probe on an optical path, i.e., an interferometer optical system.

The basic construction of the fundus camera 3000 with a coherence probe in the third embodiment will be described with reference to FIG. 9. The fundus camera 3000 with a coherence probe in the third embodiment comprises a light source 10A, a light source 10B, a light source 10C, a first dichroic mirror 11, a third dichroic mirror 12, a first lens 20, a filter 35, a windowed mirror 45, a third lens 50, a fourth lens 60, a fifth lens 70, a reference reflecting mirror 60, a sixth lens 90 and an image pickup device 700.

The light source 10A, i.e., light source 1A, emits a light beam having a short coherence length. The light source 10A employed in the third embodiment is a superluminescence diode (SLD) that emits light having a desired coherence length.

The light source 10B, i.e., light source 1B, emits light having a short coherence length. The light source 10B employed in the third embodiment is a superluminescence diode (SLD) that emits light having a desired coherence length.

The light source 10A, similarly to that employed in the second embodiment, is an SLD that emits light having a wavelength of about 0.8 µm and the light source 10B, similarly to that employed in the second embodiment, is an SLD that emits light having a wavelength of about 1.1 µm.

The light source 10C emits visible light necessary for the observation of the eyeground, such as forming an image by the image pickup device 700 comprising a camera tube or a CCD or taking photographs by a camera. The light source 10C may comprise a single light emitting element or a plurality of light emitting elements. In the third embodiment, the light source 10C is provided with a xenon lamp. The light source 10C may be of any suitable type. The light source 10C is a second light source.

The light sources 10A, 10B and 10C are disposed in a conjugate relation in terms of geometric optics with respect to the first lens 20.

When the light beams emitted respectively by the light sources 10A, 10B and 10C are completely different in wavelength distribution from each other, the filter 35 is able to separate and make common optical paths.

When only the observation of the eyeground is necessary and the eyeground need not be photographed, the light source 10B may be a light source that emits light radiations of wavelengths in the wavelength range of red rays to near-infrared rays.

When the eyeground needs to be photographed as well as to be observed, the light source 10B may be a light source that emits visible radiations. When photographing the eyeground, the pupil of the measuring eye must be dilated with a mydriatic.

Figure 9:
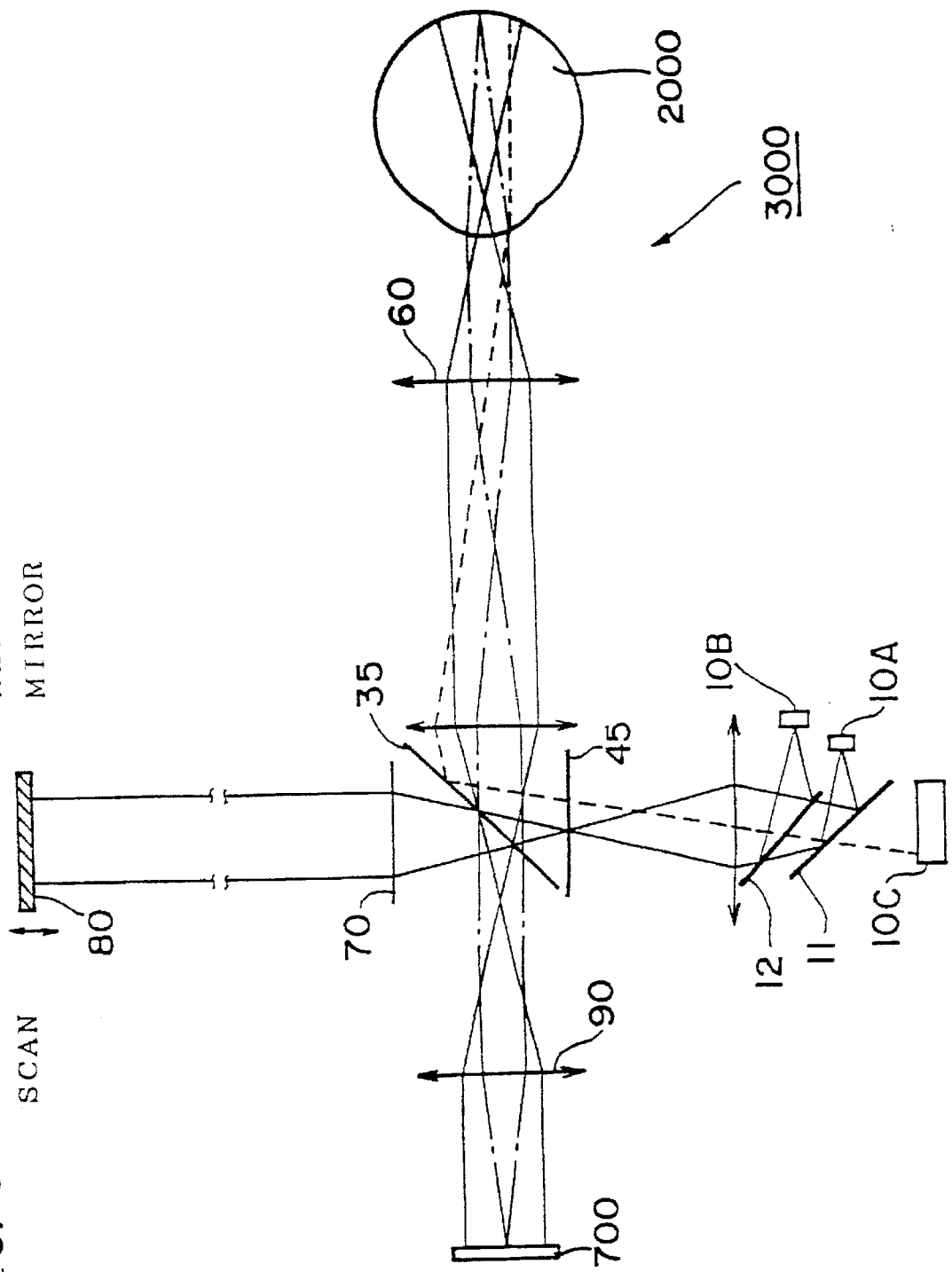
FIG. 9 is a diagrammatic view of an ophthalmometric apparatus in a third embodiment according to the present invention.

The first dichroic mirror 11 is a semitransparent mirror or, as shown in FIG. 9, an optical element that reflects only the light beam from the light source 10A and transmits the light beam from the light source 10B.

The third dichroic mirror 12 is an optical element that reflects only the light beam from the light source 10B.

The light sources 10A and 10B need not necessarily be disposed at positions specifically shown in FIG. 9; the respective positions of the light sources 10A and 10B may be inverted. When the respective positions of the light sources 10A and 10B are inverted, the positions of the first dichroic mirror 11 and the third dichroic mirror 12 must be inverted accordingly.

The light beams are projected through the first lens 20 on the filter 35. The filter 35 is an optical element having wavelength selectivity and selectively transmits light radiations of wavelengths in a specific wavelength range and reflects light rays of wavelengths outside the specific wavelength range.

Figure 10:
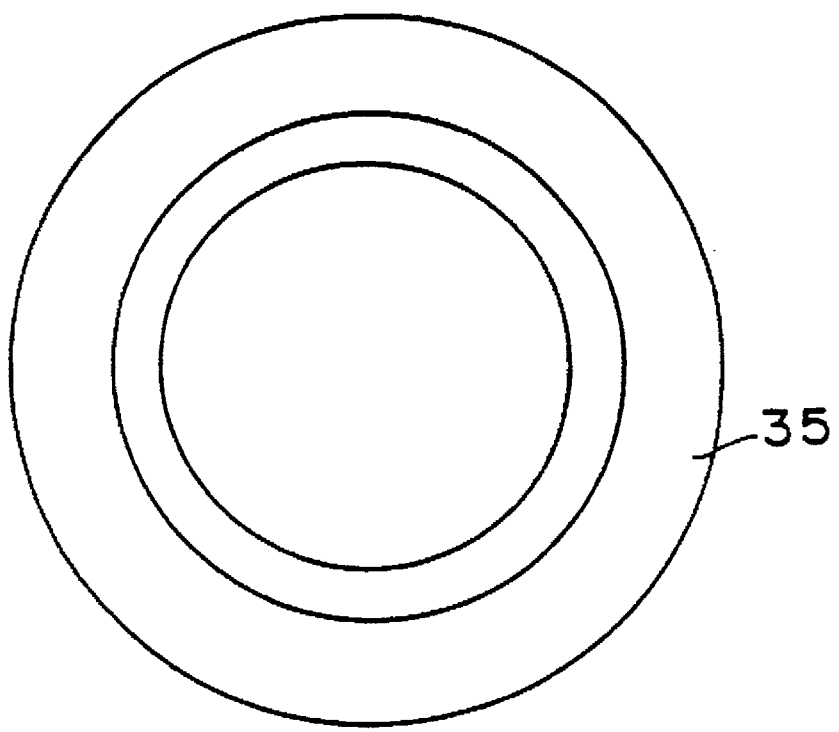
FIG. 10 is a plan view of a filter 35 included in the third embodiment.

The filter 35 will be described with reference to FIG. 10.

The entire region of the filter 35 transmits light radiations of wavelengths in the wavelength ranges of the light radiations emitted by the light sources 10A and 10B. The filter 35 has an annular region that transmits the light beam emitted by the light source 10C for the observation of the eyeground.

Since the coherence probe is an interferometer, the light beams emitted by the light sources 10A and 10B need to be split into those traveling along a measuring optical path leading to the measuring object, i.e., the eye, and those traveling along a reference optical path. The light beams are split into those traveling along the measuring optical path and those traveling along the reference optical path by the reflector or windowed mirror 45 serving as a beam splitter.

Since the respective optical paths for an annular illumination system and an image forming system of the fundus camera 3000 with a coherence probe are coaxial, the optical paths must be split by the windowed mirror 45.

The central region of the windowed mirror 45 is semitransparent to the light beams emitted by the light sources 10A and 10B, and serves as a semitransparent mirror. The central region is 100% transparent to the light beam emitted by the light source 10C for the fundus camera, and the peripheral region of the windowed mirror 45 surrounding the central region reflects the light beam emitted by the light source 10C and serves as a reflecting mirror.

Therefore only the light beam reflected by the reflecting mirror falls on the eyeground, and light rays scattered by portions around the eyeground travel through the central region of the windowed mirror 45 and fall on the image pickup device 700.

These regions are dependent on the size of the windowed mirror 45.

The construction of the optical system in the third embodiment is the same in other respects as that of the optical systems in the first and the second embodiment, and hence the description thereof will be omitted.

Figure 11:
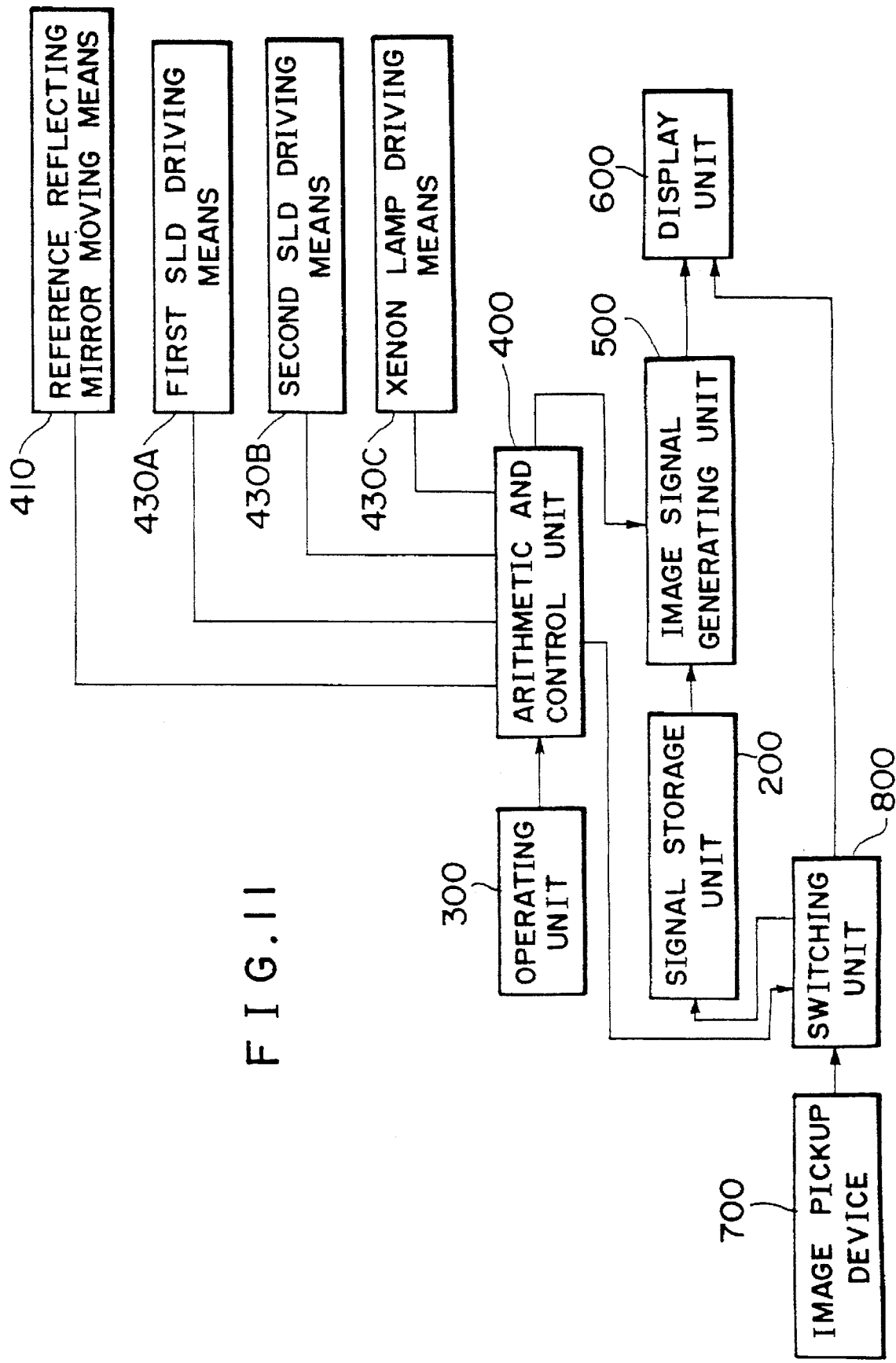
FIG. 11 is a block diagram showing the electrical configuration of the third embodiment.

The electrical configuration of the third embodiment will be described hereinafter with reference to FIG. 11.

The fundus camera 3000 with a coherence probe in the third embodiment has an electrical system comprising the image pickup device 700, a switching unit 800, a signal storage unit 200, an operating unit 300, an arithmetic and control unit 400, an image signal generating unit 500 and a display unit 600. The image pickup device 700, the signal storage unit 200 and the image signal generating unit 500 constitute an image forming unit for forming a two-dimensional image of a measuring portion.

The signal storage unit 200 stores image signals representing interference fringes and the like provided by the image pickup device 700.

The arithmetic and control unit 400 controls the general operations of the interference optical apparatus 1000, particularly, the operations of the light sources 10A, 10B and 10C and the reference reflecting mirror 80.

Connected to the arithmetic and control unit 400 are a reference reflecting mirror moving means 410, a first SLD driving means 430A, a second SLD driving means 430B and a xenon lamp driving means 430C.

The first SLD driving means 430A drives the light source 10A to make the light source 10A emit a light beam having a wavelength of about 0.8 μm. The second SLD driving means 430B drives the light source 10B to make the light source 10B emit a light beam having a wavelength of about 1.1 μm. The xenon lamp driving means 430C drives the light source 10C to make the light source 10C emit visible light rays.

The image pickup device 700 is capable of receiving image signals representing interference fringes and the like from the coherence probe, and an image of the eyeground illuminated by the light rays emitted by the light source 10C. Therefore the switching unit switches over the light sources, and switches over the eyeground observing function and the coherence probe type three-dimensional measuring function from one to the other.

The rest of the electrical configuration of the third embodiment is the same as those of the first and the second embodiment, and hence the description thereof will be omitted.

The light beam that travels through the fourth lens 60 and falls on the ocular lens (the cornea) 2100 of the eye 2000 must be focused on the pupil of the eye 2000 to enable Maxwellian view.

The fundus camera may be set at a position for Maxwellian view by a generally known method of aligning a fundus camera, which decides whether or not flare is produced or which forms an image of the light source at a position (filter 35) conjugate to the eyeground, and decides whether or not the fundus camera is aligned from the position of the image of the light source in the image of the eyeground.

Furthermore, similarly to a generally known fundus camera, when some coexistance is found in the image of the eyeground, a method of selecting a three-dimensional observation position uses the fundus camera as a monitor to find a desired position.

The fundus camera must be delicately positioned relative to the measuring eye. The adjustment of the working distance between the fundus camera and the measuring eye is important.

When adjusting the working distance, an index light source for acknowledging the status of the working distance is provided, wherein a light beam emitted by the index light source is reflected from the cornea of the measuring eye, and the working distance is adjusted so that an index is focused at a position coinciding with an image plane on which an image of the eyeground of the measuring eye is formed. Thus the working distance can be easily adjusted.

The operation of the third embodiment will be described hereinafter with reference to FIG. 12.

In step S1, the operating unit 300 is operated to actuate the arithmetic and control unit 400 to start an operation for photographing the eyeground by the fundus camera 3000 with a coherence probe.

In step S2, the fundus camera 3000 is initialized to prepare for measurement. In step S3, the arithmetic and control unit 400 drives the xenon lamp driving means 430C to turn on the light source 10C. Then, the image pickup device 700 converts an image of the eyeground into corresponding image signals in step S4.

In step S5, the image signals provided in step S4 are stored in the signal storage unit 200 and an image represented by the image signals is displayed by the display unit 600.

In step S6, a query is made to see if the observation of the eyeground has been completed and an instruction for the measurement of a section of the eyeground is given. If the instruction for the measurement of a section of the eyeground is entered step S7 is executed.

In step S7, the arithmetic and control unit 400 stops driving the xenon lamp driving means 430 to turn off the light source 10C, and drives the first SLD driving means 430A to make the light source 10A emit a light beam having a wavelength of about 0.8 μm.

In step S8, the arithmetic and control unit 400 drives the reference reflecting mirror driving means 410 to shift the reference reflecting mirror 80 to a position (measurement starting position) corresponding to k=1.

In step S9, the image pickup device 700 converts an interference image formed by the light beam emitted by the light source 10A with the reference reflecting mirror positioned at the position corresponding to k=1 into electric image signals. In step S10, the arithmetic and control unit 400 stores the image signals provided by the image pickup device 700 in step S9 in the signal storage unit 200.

In step S11, a query is made to see if k≦Z. If the response in steps S11 is negative, the value of k is incremented by one and the program returns to step S8. In step S8, the arithmetic and control unit 400 drives the reference reflecting mirror driving means 410 to shift the reference reflecting mirror 80 to a position corresponding to k=2.

The Z is a value corresponding to the depth of the front half of the measuring eye from the retina.

The foregoing steps are repeated until the reference reflecting mirror 80 is shifted to a position corresponding to k=Z, and image data thus obtained is stored in the signal storage unit 200.

When k=Z in steps S11, the arithmetic and control unit 400 stops driving the first SLD driving means 430A to turn off the light source 10A, and drives the second SLD driving means 430B to make the light source emit a light beam having a wavelength of about 1.1 µm in step S12.

In step S13, the arithmetic and control unit 400 drives the reference reflecting mirror driving means 410 to shift the reference reflecting mirror 80 to a position corresponding to k=Z+1.

In step S14, the image pickup device 700 converts an interference image formed by the light beam emitted by the light source 10B with the reference reflecting mirror 80 positioned at the position corresponding to k=Z+1 into electric image signals.

In step S15, the arithmetic and control unit 400 stores the electric image signals provided by the image pickup device 700 in step S14 in the signal storage unit 200.

In step S16, a query is made to see if k is equal to or smaller than 1000. If the response in step S16 is affirmative, the value of k is incremented by one and the program returns to step S12. Then, in step S12, the arithmetic and control unit 400 drives the reference reflecting mirror driving means 410 to shift the reference reflecting mirror 80 to a position corresponding to k=Z+2.

The foregoing steps are repeated until the reference reflecting mirror 80 is shifted to a position corresponding to k=1000, and image data thus obtained is stored in the signal storage unit 200.

The arithmetic and control unit 400 reads the image signals from the signal storage unit 200 in step S17, and the image signal generating unit 500 forms an image of a section of the eyeground in steps S18, the display unit 600 displays the image in step S19.

Then, in step S20, a query is made if measurement is to be continued. The program returns to step S2 if the response in steps S20 is affirmative or the program goes to step S21 to end measurement if the response in step S20 is negative.

The filter 35 will be concretely described below. The specifications of the filter 35 need not necessarily be limited to those mentioned below.

Basic Construction $n_s/\{(\lambda_0/8)L\ (\lambda_0/4)H\ (\lambda_0/8)L\}^m/n_0$ $n_s$: Refractive index of substrate $n_0$: Refractive index of air L: Layer of low refractive index H: Layer of high refractive index $(\lambda_0/8)$, $(\lambda_0/4)$: Thicknesses of optical films $\lambda_0$: Center wavelength m: Number of repetitions (Visible Light Transmitting Near-infrared Reflecting Filter)

$n_s$: Refractive index of substrate (Glass) n=1.5

$n_0$: Refractive index of air n=1.0

L: Layer of low refractive index $SiO_2$ (n=1.46)

H: Layer of high refractive index $TiO_2$ (n=2.30)

$\lambda_0$: Combination of a film of center wavelength=1000 nm and a film of center wavelength=1300 nm m: Number of repetitions 4 to 10 is dependent on necessity (Visible Light Transmitting Near-infrared Semi-transparent Reflecting Filter)

$n_s$: Refractive index of substrate (Glass) n=1.5

$n_0$: Refractive index of air n=1.0

L: Layer of low refractive index $SiO_2$ (n=1.46)

H: Layer of high refractive index $TiO_2$ (n=2.30)

$\lambda_0$: Center wavelength 1000 nm m: Number of repetitions 2

Fourth Embodiment

The fundus camera and the coherence probe of the fundus camera 30000 with a coherence probe in the third embodiment are not able to be used simultaneously for measurement. A fundus camera 3000 with a coherence probe in a fourth embodiment does not need the switching over of light sources.

Figure 13:
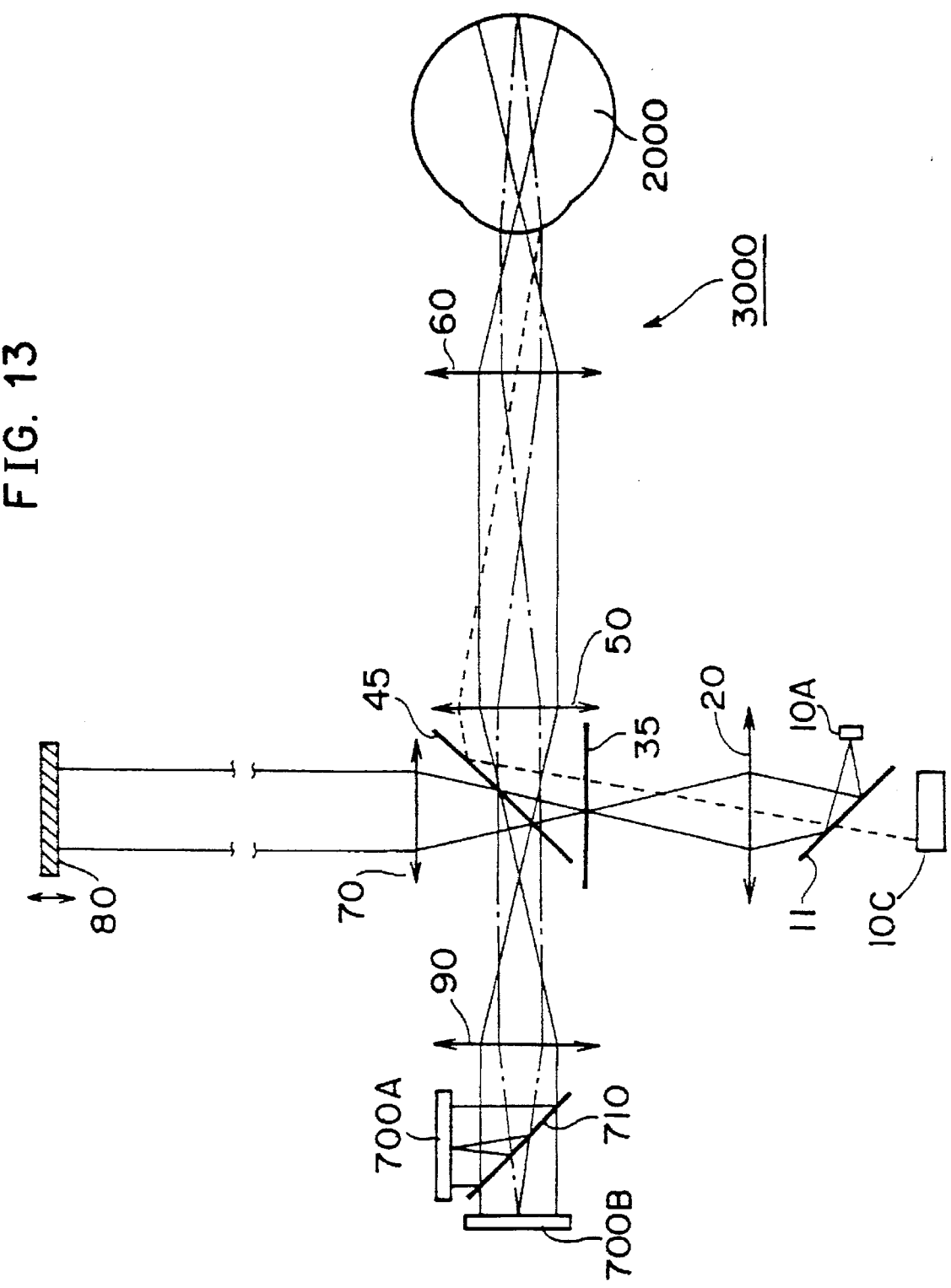
FIG. 13 is a diagrammatic view of an ophthalmometric apparatus in a fourth embodiment according to the present invention.

The basic construction of the fundus camera 3000 with a coherence probe in the fourth embodiment will be described with reference to FIG. 13. The fundus camera 3000 with a coherence probe in the fourth embodiment comprises a light source 10A, a light source 10C, a first dichroic mirror 11, a first lens 20, a filter 35, a windowed mirror 45, a third lens 50, a fourth lens 60, a fifth lens 70, a reference reflecting mirror 80, a sixth lens 90, a first image pickup device 700A, a second image pickup device 700B and a fourth dichroic mirror 710.

The fourth embodiment is not provided with any light source corresponding to the light source 10B and only the light source 10A serves as an interference light source. The fourth embodiment is provided with two image pickup devices, i.e., the first image pickup device 700A and the second image pickup device 700B.

The fourth dichroic mirror 710 forms an image of interference fringes formed by the light beam emitted by the light source 10A on the first image pickup device 700A, and an image formed by the light beam emitted by the light source 10C is formed on the second image pickup device 700B.

Thus the fourth dichroic mirror 710 selectively separates the light beam of the coherence probe and that of the fundus camera by wavelength for observation.

The fundus camera 3000 may be provided additionally with an optical path for photographing the eyeground.

In the fourth embodiment, the coherence probe and the fundus camera are able to function simultaneously for measurement.

The construction of the optical system, the electrical configuration and the operations of the fourth embodiment are the same in other respects as those of the first to the third embodiment, and hence the description thereof will be omitted.

Fifth Embodiment

A fundus camera 3000 with a coherence probe in a fifth embodiment is provided with light sources which are not disposed in a conjugate positional relation.

Figure 14:
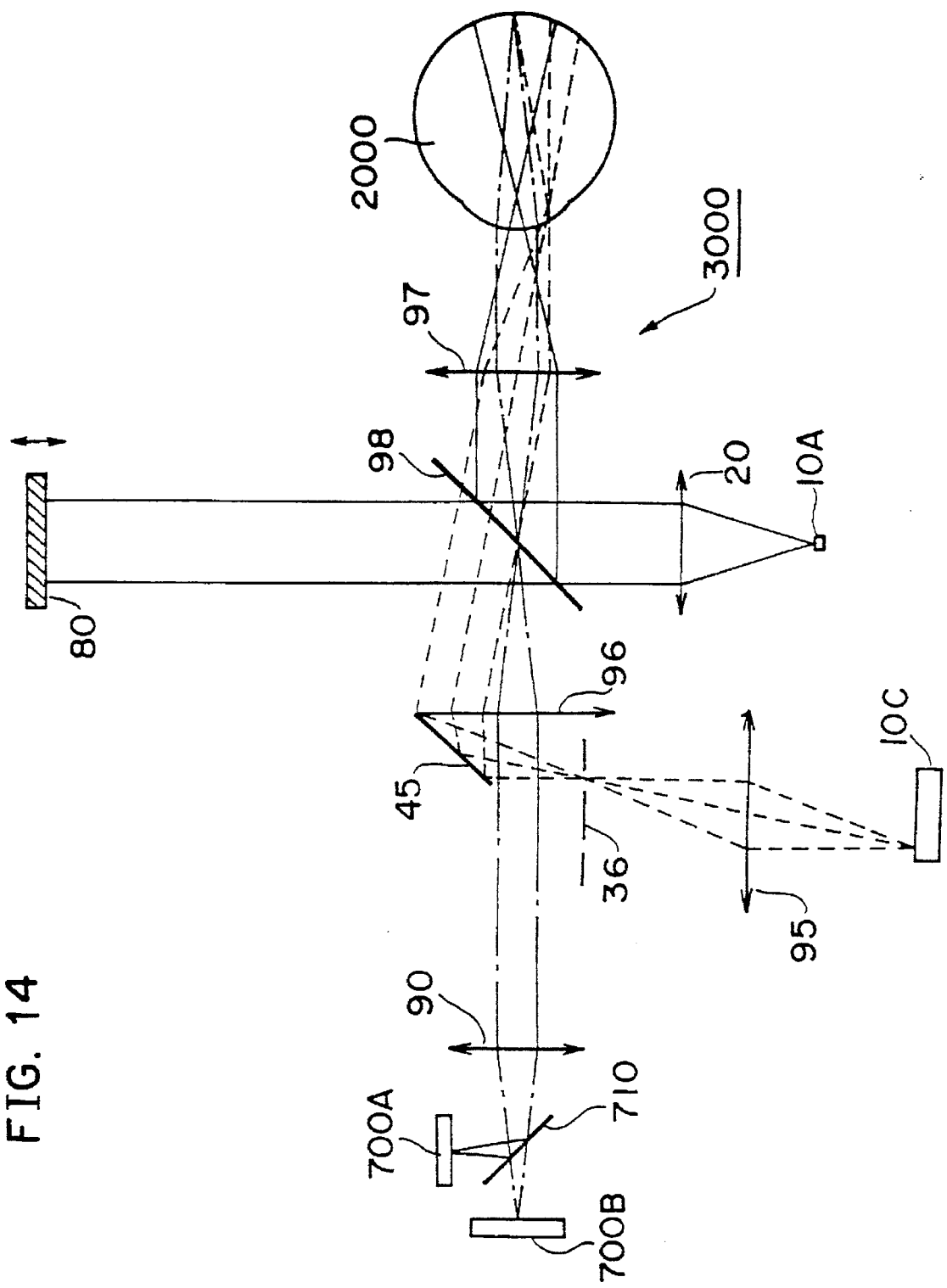
FIG. 14 is a diagrammatic view of an ophthalmometric apparatus in a fifth embodiment according to the present invention.

The basic construction of the fundus camera 3000 with a coherence probe in the fifth embodiment will be described with reference to FIG. 14. The fundus camera 3000 with a coherence probe comprises a light source 10A, a light source 10C, a first lens 20, a ring slit 36, a windowed mirror 45, a reference reflecting mirror 80, a sixth lens 90, a seventh lens 95, an eighth lens 96, a ninth lens 97, an optical element 98, a first image pickup device 700A, a second image pickup device 700B and a fourth dichroic mirror 710.

The first lens 20 is a collimator lens for the coherence probe, the seventh lens 95 forms an image of the light source 10C on the ring slit 36.

The eighth lens 96 adjust the front and the back focal point to the position of the ring slit 36. The ninth lens 97 is disposed at a distance equal to the sum of the focal lengths of the eighth lens 96 and the ninth lens 97 from the eighth lens 96.

The optical element 98 is semitransparent to the light beam emitted by the light source 10A and is 100% transparent to the light beam emitted by the light source 10C.

The first image pickup device 700A and the second image pickup device 700B are disposed behind the sixth lens 90. The fourth dichroic mirror 710, which has wavelength-selective reflecting and transmitting characteristics, forms an image of interference fringes and the like formed by the light beam emitted by the light source 10A on the first image pickup device 700A, and forms an observation image formed by the light beam emitted by the light source 10C on the second image pickup device 700B.

The fifth embodiment thus constructed is capable of obtaining images formed respectively by the coherence probe and the fundus camera.

The construction of the optical system, the electrical configuration and operations of the fifth embodiment are the same in other respects as those of the first to the fourth embodiment, and hence the description thereof will be omitted.

Modification

Figure 15:
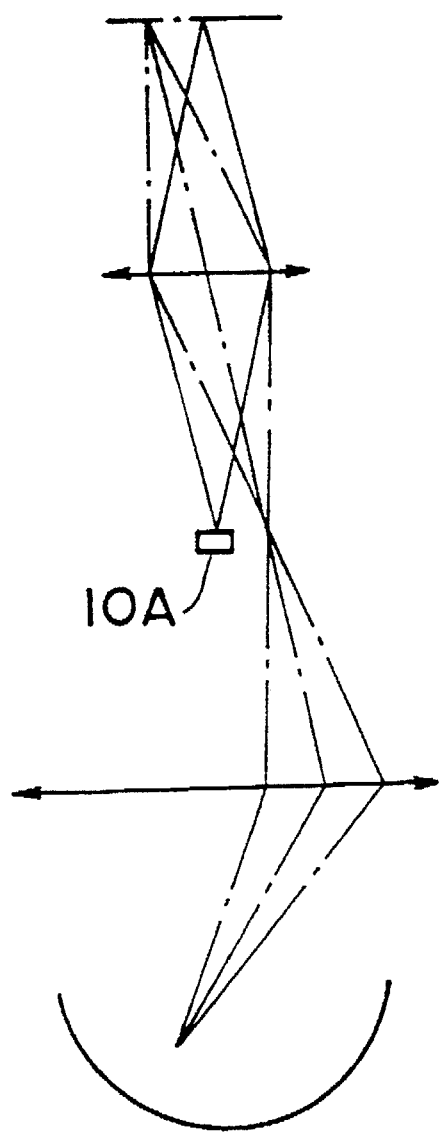
FIG. 15 is a diagrammatic view of assistance in explaining a modification.

The light source 10A may be disposed coaxially as shown in FIG. 15. The optical element 98 and such may be disposed at a conjugate position in terms of geometric optics such as the same position as the light source 10A.

As is apparent from the foregoing description, according to the present invention, the first light source emits light rays having a comparatively short coherence length, the measuring optical system converges the light rays emitted by the first light source on a position substantially corresponding to the pupil of the measuring eye and illuminates a predetermined range in a measuring portion of the measuring eye by the light rays emitted by the first light source, the beam splitter splits the reference optical path from the measuring optical path of the measuring optical system, the reference optical system including the reflection mirror capable of being moved along the optical axis of the reference optical path reflects the reference light beam, the interference optical system combines the reflected measuring light beam, and the reflected reference light beam reflected by the reference optical system for interference, the image pickup device having a plurality of image sensing elements arranged in a substantially conjugate relation with the measuring portion receives the interference light beam provided by the interference optical system, and the image signal generating unit generates image signals representing a section of a portion of the measuring eye from the output signals of the image pickup device provided when the reflecting mirror is shifted. Thus the present invention provides an ophthalmometric apparatus capable of quick measurement and of facilitating the observation of the measuring portion in the measuring eye.

Furthermore, according to the present invention, the first light source emits light rays having a comparatively short coherence length. The apparatus further includes an eyeground image optical system having a second light source and an eyeground image forming unit. The second light source emits visible light rays, the beam splitter splits the light rays emitted by the first light source into a measuring light beam that travels along the measuring optical path and a reference light beam that travels along the reference optical path, the measuring optical system illuminates the measuring eye through the optical element having a peripheral portion around the optical axis that transmits the light beam emitted by the second light source and a central portion about the optical axis that transmits the light beam emitted by the first light source so as to enable Maxwellian view and receives the reflected measuring light beam reflected from the measuring portion, the reference optical system including the reflecting mirror capable of being moved along the optical axis of the reference optical path reflects the reference light beam, the interference optical system combines the reflected measuring light beam of the measuring optical system and the reflected reference light beam of the reference optical system for interference, the image pickup device having a plurality of image sensing elements arranged so as to be conjugate to the measuring portion receives the interference light beam provided by the interference optical system, the eyeground image forming unit receives the reflected measuring light beam, i.e., the light beam emitted by the second light source, of the measuring optical system to form a two-dimensional image of the measuring portion, the image signal generating unit generates image signals representing a section of he measuring eye from the output signals of the image pickup device when the reflecting mirror is shifted on the basis of the light beam emitted by the first light source.

In accordance with the present invention, the first light source that emits light rays having a comparatively short coherence length has a light emitting element 1A that emits light rays having a shorter wavelength and a light emitting element 1B that emits light rays having a longer wavelength, and the image signal generating unit generates first color signals from the output signals provided by the image pickup device through the detection of the light beam emitted by the light emitting element 1A, and second color signals from the output signal provided by the image pickup device through the detection of the light beam emitted by the light emitting element 1B to display an image of a section of the measuring eye.

Still further, in accordance with the present invention, the image signal generating unit may generate image signals representing the section of the front half of the measuring eye from the output signal of the image pickup device provided through the detection of the light beam emitted by the light emitting element 1A of the first light source, and an image signals representing the section of the back half of the measuring eye from the output signals of the image pickup device provided through the detection of the light beam emitted by the light emitting element 1B of the first light source.

The image pickup device of the present invention may be disposed at a position conjugate to the measuring portion.

The coherence length of the light rays to be emitted by the first light source may be 40 μm or below.

What is claimed is:

1. An ophthalmometric apparatus for generating an image of a section and a surface of an eyeground of an eye of a subject having an ocular lens with a center portion and a peripheral portion, comprising:

an interference optical beam system having,
   a first light source which emits a first light beam having a short coherence length,
   a reference reflector,
   a measuring optical system for leading the first light beam to the eyeground, said first light beam being reflected off the eyeground,
   a reference optical system having an optical axis for leading the first light beam to the reference reflector, the reference reflector being movable along the optical axis of the reference optical system, said first light beam being reflected off the reference reflector, and an interference signal forming device for forming an interference signal with the first light beam reflected from the measuring optical system and the first light beam reflected from the reference optical system; and an eyeground image optical system having,
a second light source which emits a second light beam for illuminating the eyeground, the second light beam being reflected off the eyeground, and an eyeground image forming device for forming an eyeground image signal with the second light reflected from the eyeground.

2. An ophthalmometric apparatus according to claim 1, wherein the first light beam has a first wavelength, and the second light beam has a second wavelength, the first wavelength being different from the second wavelength.

3. An ophthalmometric apparatus for generating an image of a section and a surface of an eyeground of an eye of a subject having an ocular lens with a center portion and a peripheral portion, comprising:

an interferometer optical system having
a first light source which emits a first light beam having a short coherence length,
a reference reflector, and
a coherent probe optical path for leading the first beam of light to the eyeground and to the reference reflector, the reference reflector being movable along the coherent probe optical path,
a interference signal forming device for forming an interference signal with the first light from the coherent optical path; and an eyeground image optical system having
a second light source which emits a second light beam for illuminating the eyeground, the second light beam being reflected from the eyeground, and an eyeground image signal forming device for forming an eyeground image signal from the reflected second beam of light.

4. An ophthalmometric apparatus according to claim 3, wherein the first light beam has a first wavelength, and the second light beam has a second wavelength, the first wavelength being different from the second wavelength.

5. An ophthalmometric apparatus according to claim 4, wherein the interferometer optical system and the eyeground image optical system have at least one common element, said at least one common element being an optical element having wavelength selectivity.

6. An ophthalmometric apparatus according to claim 5, wherein the optical element is a reflector.

7. An ophthalmometric apparatus according to claim 6, the reflector having a central region and a peripheral region, the central region being semitransparent to the first light beam and transparent to the second light beam, and the peripheral region reflecting the second light beam.

8. An ophthalmometric apparatus according to claim 5, wherein the optical element is a filter having an annular region.

9. An ophthalmometric apparatus according to claim 8, wherein the filter transmits the first light beam, and transmits the second light beam only through the annular region.

10. An ophthalmometric apparatus according to claim 7 or 9, wherein the measuring optical system projects the first light beam to the eyeground through the center region of the ocular lens, and the eyeground image optical system illuminates the eyeground through the peripheral region of the ocular lens.

11. An ophthalmometric apparatus for generating an image of a section and a surface of an eyeground of an eye of a subject having an ocular lens with a central portion and a peripheral portion, comprising:

a first light source which emits a first light beam having a short coherence length,
a second light source which emits a second light beam,
a first optical system leading the first light beam and the second light beam to the eyeground, and receiving the first light beam and the second light beam after being reflected from the eyeground,
a reference reflector,
a second optical system having an optical axis for leading the first light beam to the reference reflector, the first light beam being reflected off the reference reflector, the reference reflector being movable along the optical axis of the second optical system,
an interference forming signal device for forming an interference signal with the first light beam reflected from the eyeground and the first light beam reflected from the reference reflector, and
an eyeground image signal forming device for forming an eyeground image signal with the second light beam reflected from the eyeground.

12. An ophthalmometric apparatus according to claim 11, wherein the first light beam has a first wavelength, and the second light beam has a second wavelength, the first wavelength being different from the second wavelength.

13. An ophthalmometric apparatus according to claim 12, further comprising an optical element having wavelength selectivity.

14. An ophthalmometric apparatus according to claim 13, the optical element having a central region and a peripheral region, the central region being semitransparent to the first light beam and transparent to the second light beam, and the peripheral region reflecting the second light beam.

15. An ophthalmometric apparatus according to claim 14, wherein the measuring optical system projects the first light beam to the eyeground through the center region of the ocular lens, and the eyeground image optical system illuminates the eyeground through the peripheral region of the ocular lens.

16. An ophthalmometric apparatus for generating an image of a section and a surface of an eyeground of an eye of a subject having an ocular lens with a center region and a peripheral region comprising:

an interference optical system having a first light source which emits a first light beam having a short coherence length,
a reference reflector,
a measuring optical system for projecting the first light beam to the eyeground through the center region of the ocular lens,
a reference optical system having an optical axis for projecting the first light beam to the reference reflector, the reference reflector being movable along the optical axis of the reference optical system, and
an interference signal forming device for forming an interference signal with the first light from the measuring optical system and from the reference optical system;

an eyeground image optical system having
a second light source which emits a second light beam for illuminating the eyeground of the subject, an illuminating optical system for illuminating the eyeground of the subject through the peripheral region of the ocular lens, and an eyeground image signal forming device for forming an eyeground image signal with the second light reflected from the eyeground.

17. An ophthalmometric apparatus according to claim 16, wherein the first light beam has a first wavelength, and the second light beam has a second wavelength, the first wavelength being different from the second wavelength.

18. An ophthalmometric apparatus for generating an image of a section and a surface of an eyeground of an eye of a subject having an ocular lens with a central region and a peripheral region, comprising:

an interferometer optical system having a first light source which emits a first light beam having a short coherence length, a reference reflector, a coherent probe optical system having an optical axis for leading the first light to the eyeground through the center region of the ocular lens and to the reference reflector, the reference reflector being movable along the optical axis of the coherent probe optical system, and a interference signal forming device for forming an interference signal with the first light through the coherent probe optical system; and an eyeground image optical system having a second light source which emits a second light beam for illuminating the eyeground, an illuminating optical system for illuminating the eyeground through the peripheral region of the ocular lens, and an eyeground image signal forming device for forming an eyeground image signal from the reflected second beam of light.

19. An ophthalmometric apparatus according to claim 18, wherein the first light beam has a first wavelength, and the second light beam has a second wavelength, the first wavelength being different from the second wavelength.

20. An ophthalmometric apparatus according to claim 19, wherein the interferometer optical beam system and the eyeground image optical system have at least one common element, said common element being an optical element having wavelength selectivity.

21. An ophthalmometric apparatus according to claim 20, wherein the optical element is a reflector.

22. An ophthalmometric apparatus according to claim 21, the reflector having a central region and a peripheral region, the central region being semitransparent to the first light beam and transparent to the second light beam, and the peripheral region reflecting the second light beam.

23. An ophthalmometric apparatus according to claim 20, wherein the optical element is a filter.

24. An ophthalmometric apparatus according to claim 23, wherein the filter transmits the first light beam through and transmits the second light beam only through an annular region.

* * * * *